US006346280B1

(12) United States Patent
Castillo et al.

(10) Patent No.: US 6,346,280 B1
(45) Date of Patent: *Feb. 12, 2002

(54) COMPOSITION AND METHODS FOR INHIBITING THE FORMATION OF BRAIN AMYLOID DEPOSITS

(75) Inventors: Gerardo Castillo, Seattle; Alan D. Snow, Lynnwood, both of WA (US)

(73) Assignee: University of Washington, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/198,824

(22) Filed: Nov. 24, 1998

Related U.S. Application Data

(63) Continuation-in-part of application No. 09/079,829, filed on May 15, 1998.
(60) Provisional application No. 60/046,602, filed on May 15, 1997.

(51) Int. Cl.⁷ ............................................... A61K 35/78

(52) U.S. Cl. ...................... 424/725; 424/773; 424/775

(58) Field of Search ............................. 424/195.1, 725, 424/775, 773

(56) References Cited

U.S. PATENT DOCUMENTS 4,844,901 A  * 7/1989  Keplinger et al.
4,940,725 A  * 7/1990  Keplinger et al.
5,166,139 A    11/1992 Bombardelli et al.
5,302,611 A  * 4/1994  Keplinger et al.

OTHER PUBLICATIONS

Derwent English abstract of Russian Patent No. 2,076,731 C1; Getmanskaya et al., Apr. 10, 1997.*
Braquet et al. "Ethnopharmacology and the Development of Natural PAF Antagonists as Therapeutic Agents," Journal of Ethnopharmacology, vol. 32, pp. 135–139, 1991.
Ho et al. "Phytochemicals in Teas and Rosemary and Their Cancer–Preventive Properties," ACS Symp. Ser. (Food Phytochemicals for Cancer Prevention II) vol. 547, pp. 2–19 1994.
Jain et al. "Antiinflammatory Effects of an Ayurvedic Preparation, Brahmi Rasayan, in Rodents," Indian Journal of Experimental Biology, vol. 32, pp. 633–636, Sep. 1994.
Benson et al. "Serum Amyloid a Protein in Amyloidosis, Rheumatic, and Neoplastic Diseases," Arthritis and Rheumatism, vol. 22, No. 1, pp. 36–42, Jan. 1979.
Kamei et al. "Amyloidosis Associated with Juvenile Rheumatoid Arthritis," Acta Pathol. Jpn., vol. 32, No. 1, pp. 23–33, 1982.

Mcadam et al. "Association of Amyloidosis with Erythema Nodosum Leprosum Reactions and Recurrent Neutrophil Leucocytosis in Leprosy", The Lancet, pp. 572–576, Sep. 27, 1975.
Metaxis et al. "Familial Mediterranean Fever and Amyloidosis", Kidney International, vol. 20, pp. 676–685, 1981.
Harada et al. "Human Amyloid Protein: Chemical Variability and Homogeneity", Journal of Histochemistry and Cytochemistry, vol. 19, No. 1, pp. 1–115, Jun. 1970.
Johnson et al. "Islet Amyloid, Islet–Amyloid Polypeptide, and Diabetes Mellitus", The New England Journal of Medicine, vol. 321, No. 8, pp. 513–518, Aug. 24, 1989.
Johnson et al. "Islet Amyloid Polypeptide: Mechanisms of Amyloidogenesis in the Pancreatic Islet and Potential Roles in Diabetes Mellitus", Laboratory Investigation, vol. 66, No. 5, pp. 522–534, 1992.
Gejyo et al. "A New Form of Protein Associated with Chronic Hemodialysis was Identified as B2 Metroglobulin", Biochemical and Biophysical Research Communications, vol. 129, No. 3, pp. 701–706, 1985.
Gejyo et al. "B2–Metroglobulin: A New From of Protein Associated with Chronic Hemodialysis", Kidney International, vol. 30, pp. 385–390, Jan. 1986.
Skinner et al. "The Prealbinum Nature of the Amyloid Protein in Familial Amyloid Polyneuropathy (FAP)–Swedish Variety", Biochemical and Biophysical Research Communications, vol. 99, No. 4, pp. 1326–1332, Apr. 1981.
Saraiva et al. "Studies on Plasma Transthyretin (Prealbinum) in Familial Amyloidotic Polyneropathy, Portugese Type", Department of Medicine, Columbia University Colleg of Physicians and Surgeons, vol. 102, No. 4, pp. 590–603, Jun. 1983.
Saraiva et al. "Amyloid Fibral Protein in Familial Amyloidotic Polyneurotherapy, Portugese Type", The American Society for Clinical Investigation, Inc., vol. 74, pp. 104–119, Jul. 1984.
Tawara et al. "Amyloid Fibril Protein in Type 1 Familial Amyloidotic Polyneurotherapy in Japanese", Laboratory of Clinical Investigation, vol. 98, No. 6, pp. 811–822, Dec. 1981.
"Progress Report on Alzheimers Disease", The National Institute on Aging, National Institutes of Health, 1997, 'author and complete publishing data unknown'.
Cutler et al. "Correspondence: Tacrine in Alzheimers Disease", The New England Journal of Medicine, pp. 808–810, Mar. 1993.
Barner et al. "Donepezil Use in Alzheimer Disease", The Annals of Pharmacotherupy, vol. 32, pp. 70–77, Jan. 1998.

(List continued on next page.)

Primary Examiner—Francisco Prats
Assistant Examiner—Susan D. Coe
(74) Attorney, Agent, or Firm—Patrick M. Dwyer

(57) ABSTRACT

A method for treating brain amyloid deposits and the symptoms and conditions associated with brain amyloid deposits using the plant Uncaria tomentosa and extracts therefrom

5 Claims, 10 Drawing Sheets

OTHER PUBLICATIONS

Glenner et al. "Alzheimer's Disease: Initial Report of the Purification and Characterization of a Novel Cerebrovascular Amyloid Protein," Biochemical and Biophysical Research Communications, vol. 120, No. 3, pp. 885–890, May 16, 1984.

Masters et al. "Amyloid Plaque Core Protein in Alzheimers Disease and Down Syndrome," Medical Sciences, vol. 82, pp. 4245–4249, Jun. 1983.

Husby et al. "Nomenclature of Amyloid and Amyloidosis," Bulletin of the World Health Organization, vol. 71, No. 1, pp. 105–108, 1993.

Tanzi et al. "Protein Inhibitor Domain Encoded by an Amyloid Protein Precursor mRNA Associated with Alzheimer's Disease," Nature, vol. 331, pp. 528–532, Feb. 1988.

Kitaguchi et al. "Novel Precursor of Alzheimer's Disease Amyloid Protein Shows Protease Inhibitory Activity," Nature, vol. 331, pp. 530–532, Feb. 1988.

Ponte et al. "A New A4 Amyloid mRNA Contains a Domain Homologous to Serine Proteinase Inhibitors," Nature, vol. 311, pp. 525–527, Feb. 1988.

Grundke–Iqbal et al. "Abnornal Phosphorylation of the Microtubule–Associated Protein Tau Alzheimer Cytoskeletal Pathology,"Proc. Natl. Acad. Sci. USA, vol. 83, pp. 4913–4917, Jul. 1986.

Kosik et al. "Microtubule—Associated Protein Tau is a Major Antigenic Component of Pairedd Helicule Filaments in Alzheimer's Disease," Proc. Natl. Acad. Sci. USA, vol. 83, pp. 4044–4048, Jun. 1986.

Lee et al. "A68: A Major Subunit of Paired Helical Filaments and Derivatized Forms of Normal Tau," Science, vol. 251, pp. 675–678, Feb. 1991.

Mandybur et al. "Cerebral Amyloid Angiopathy: The Vascular Pathology and Complications," Journal of Neuropathology and Experimental Neurology, vol. 45, No. 1, pp. 79–90, Jan. 1986.

Pardridge et al. "Amyloid Angiopathy of Alzheimer's Disease: Amino Acid Composition and Partial Sequence of a 4,200–Dalton Peptid Isolated from Cortical Microvessels," Journal of Neurochemisty, vol. 49. No. 5, pp. 1394–1401, 1987.

Pike et al. "In Vitro Aging of B–Amyloid Protein Cause Peptide Aggregation and Neurotoxity," Brain Research, vol. 563, pp. 311–314, 1991.

Pike et al. "Structure–Activity Analyses of B–Amyloid Peptides: Contributions of the B25–35 Region to Aggregation and Neurotoxicity," Journal of Neurochemisty, vol. 64, No. 1, pp. 253–265, 1995.

Harrigan et al. "Beta Amyloid is Neurotoxic in Hippocampal Slice Cultures," The Neurobiology of Aging, vol. 16, No. 5, pp779–789, 1995.

Games et al. "Alzheimer–type neuopathology in transgenic mice overexpressing V717F B–amyloid precursor protein." Nature, vol. 373, p. 523–527, Feb. 9, 1995.

Hsiao et al. "Age–related CNS Disorder and early death in transgenic FVB/N mice overexpressing alsheimer amyloid precursor proteins."Neuron, vol. 15, 1203–1218, Nov., 1995.

Flood et al "Amnestic effects in mice of four synthetic peptides homologous to amyloid B protein from patients wit alzheimer disease." Proc. Natl. Acad. Sci. USA, vol. 88, pp. 3363–3366, Apr. 1991.

Flood et al. "An amyloid B–protein fragment, AB[12–18], equipotently impairs post–training memory processing when injected into different limbic system structures." Brain Research 663 (1994).

Broeckhoven et al. "Amyloid B Protein precursor gene and Hereditary cerebral hemorrage with amyloidosis (Dutch)." Science, vol. 248, pp. 1120–1122. 1990.

Murrell et al. "A mutation in the amyloid recursor protein associated with hereditary alzheimer's disease." Reports, pp. 97–99, Oct. 4, 1991.

Haass et al. "The swedish mutation causes early–onset alzheimer's disease by B–secretase cleavage with in the secretory pathway." Nature medicine, vol. 1, No. 12, Dec. 1995.

Steinberg. "*Uncaria Tomentosa* (cat's Claw) A wondrous herb from the peruvian rain forest." Townsend letter for doctors–pp, 442–443, may 1994.

Naiki et al. "Hinetic analysis of amyloid Fibril polymerization in vitro."Laboratory Investigation, vol. 65, No. 1, p. 104, 1991.

Levine. "Thioflavine T interaction with synthetic alzheimer's disease B–amyloid peptides: Detection of amyloid aggregation in solution."Protein Science, 2, 404–410, 1993.

Levine. "Thioflavine T interacton with amyloid B–sheet structures."Amyloid: Int. J. Exp. Clin. Invest. 2, 1–6, 1995.

Naiki. "First order kinetic model of alzheimer's B–amyloid fibril extension in vitro."Laboratory investigation, vol. 74, No. 2, p. 374, 1996.

Snow. "Proteoplycans in the pathogenesis of alzheimer's disease and other amyloidoses."Meurobiology of Aging, vol. 10, pp. 481–497, 1989.

Castillo. "Perlecan Binds to the B–amyloid proteins (AB) of alzheimer's desiase, Accelerates AB fibril formation, and Maintains AB fibril Stability."Journal of Neurochemistry, vol. 69, No. 6, pp. 2452–2465, 1997.

Castillo. "Novel Purification and detailed characterization of perlecan isolated from the engelbreth–holm–swarm tumor for use in an animal model of fibrillar AB amyloid persistence in brain."J. Biochen. vol. 120, No. 2, pp. 433–444, 1996.

Tamaoka et al. "Amyloid B protein 1–42/43(AB 1–42/43) in crebellar diffuse plaques: enzyme–linked immunosorbent assay and immunocytochemical study."Brain Research 679 (1995) 151–156.

Tamaoka et al. "Biochemical evedence for the long tail form of amyloid B protein as a seed molecule in cerebral deposits of alzheimer's disease."Biochemical and biophysical research communications, vol. 205, No. 1, pp. 834–842, 1994.

Cooper et al. "Purification and characterization of a peptide from amyloid–rich pancreases of type 2 diabetic patients."Proc. Natl. Acad. Sci. USA, vol. 84, pp. 8628–8632, Dec. 1987.

Castillo et al. "Sulfate content and specific glycosaminoglycan backbone of perlecan are critical of perlecan't enhancement of islet amyloid polypeptide (Amylin) Fibril formation."Diabetes, vol. 47, pp. 612–620, Apr. 1998.

* cited by examiner

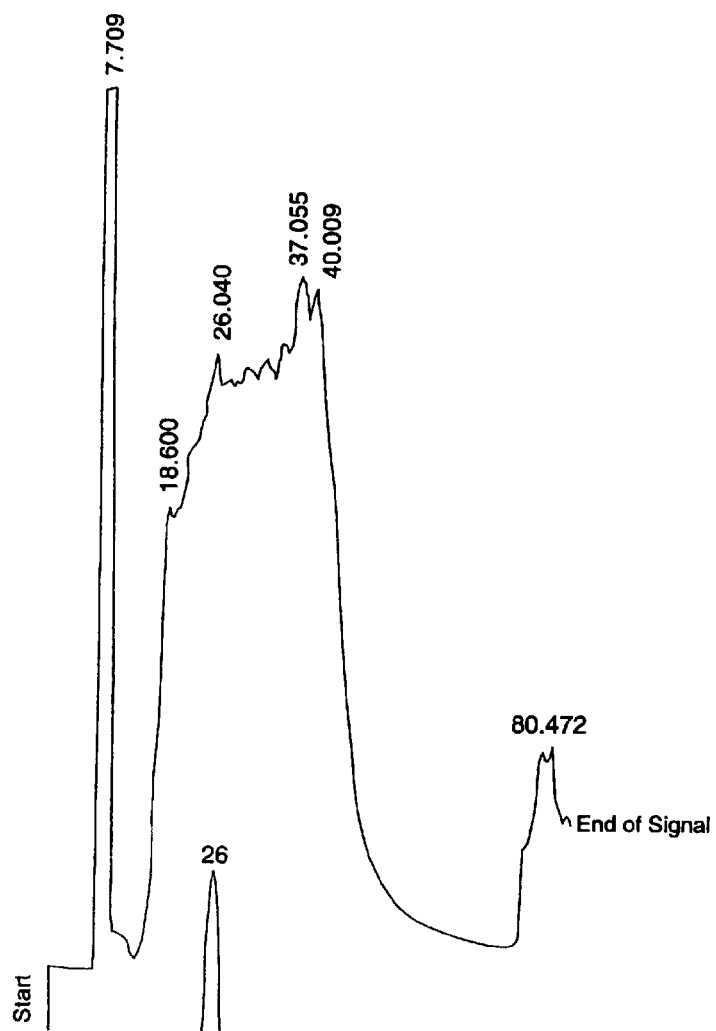
FIGURE 10a
A.
FIGURE 10b
B.
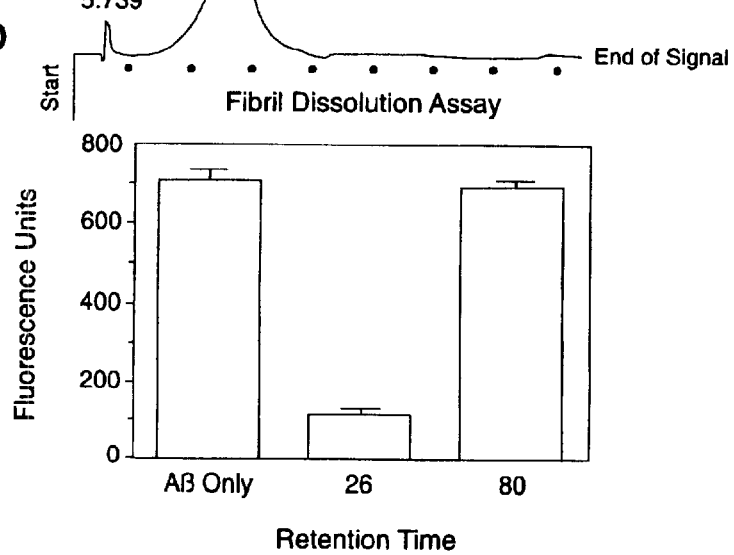
FIGURE 10c
C.

COMPOSITION AND METHODS FOR INHIBITING THE FORMATION OF BRAIN AMYLOID DEPOSITS

This application is a continuation-in-part of U.S. patent application Ser. No. 09/079,829 filed May 15, 1998, which claimed priority to provisional patent application Ser. No. 60/046,602 filed May 15, 1997; no patenting or abandonment of the parent application has occurred.

TECHNICAL FIELD

The invention relates to compositions and methods for treating Alzheimer's Disease and other amyloidoses, and to methods for isolating pharmacological agents from plant matter; more particularly, it relates to compositions and methods for therapeutic intervention in Alzheimer's disease and other amyloidoses and methods for isolation of and identification of amyloid inhibitory ingredients within plant matter.

BACKGROUND OF THE INVENTION

Alzheimer's disease is characterized by the accumulation of a 39–43 amino acid peptide termed the beta-amyloid protein or A$\beta$, in a fibrillar form, existing as extracellular amyloid plaques and as amyloid within the walls of cerebral blood vessels. Fibrillar A$\beta$ amyloid deposition in Alzheimer's disease is believed to be detrimental to the patient and eventually leads to toxicity and neuronal cell death, characteristic hallmarks of Alzheimer's disease. Accumulating evidence implicates amyloid as a major causative factor of Alzheimer's disease pathogenesis.

A variety of other human diseases also demonstrate amyloid deposition and usually involve systemic organs (i.e. organs or tissues lying outside the central nervous system), with the amyloid accumulation leading to organ dysfunction or failure. In Alzheimer's disease and "systemic" amyloid diseases, there is currently no cure or effective treatment, and the patient usually dies within 3 to 10 years from disease onset.

Much work in Alzheimer's disease has been accomplished, but little is conventionally known about compounds or agents for therapeutic regimes to arrest amyloid formation, deposition, accumulation and/or persistence that occurs in Alzheimer's disease and other amyloidoses.

New compounds or agents for therapeutic regimes to arrest or reverse amyloid formation, deposition, accumulation and/or persistence that occurs in Alzheimer's disease and other amyloidoses are therefore desperately needed.

DISCLOSURE OF THE INVENTION

A primary object of the present invention is to establish new methods for the treatment of the amyloid diseases. The amyloid diseases include, but are not limited to, the amyloid associated with Alzheimer's disease, Down's syndrome and hereditary cerebral hemorrhage with amyloidosis of the Dutch type (wherein the specific amyloid is referred to as beta-amyloid protein or A$\beta$), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

Another object of the present invention is to use the inner bark and/or roots from *Uncaria tomentosa* (also referred to as Uña de Gato or Cat's claw) for the treatment of amyloid formation, deposition, accumulation and/or persistence in Alzheimer's disease, type II diabetes and other amyloidoses. *Uncaria tomentosa* or Cat's claw is also referred to as, but not limited to, Paraguayo, Garabato, Garbato casha, Tambor huasca, Una de gavilan, Hawk's claw, Nail of Cat, and Nail of Cat Schuler.

Another object of the present invention is to use extracts and/or derivatives thereof from plant matter related to the Rubiciaceae family, which includes but is not limited to the Uncaria genus, for the treatment of amyloid formation, deposition, accumulation and/or persistence in Alzheimer's disease, type II diabetes and other amyloidoses.

Another object of the present invention is to use extracts and/or derivatives thereof from plant matter related to the various Uncaria species, which may include but not limited to, *Uncaria tomentosa, Uncaria attenuata, Uncaria elliptica, Uncaria guianensis, Uncaria pteropoda, Uncaria bernaysli, Uncaria ferra DC, Uncaria kawakamii, Uncaria rhyncophylla, Uncaria calophylla, Uncaria gambir*, and *Uncaria orientalis*.

Another object of the present invention is to use commercially available pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, bark bundles and/orb ark powder which contain Uncaria tomentosa to treat patients with Alzheimer's disease, type II diabetes and other amyloidoses.

Another object of the present invention is to use *Uncaria tomentosa* and/or the oxindole alkaloids contained within *Uncaria tomentosa* for the treatment of amyloid formation, deposition, accumulation and/or persistence in Alzheimer's disease, type II diabetes and other amyloidoses.

Yet another object of the present invention is to use the quinovic acid glycosides contained within *Uncaria tomentosa* for the treatment of amyloid formation, deposition, accumulation and/or persistence in Alzheimer's disease, type II diabetes and other amyloidoses.

Yet another object of the present invention is to use the proanthocyanidins contained within *Uncaria tomentosa* for the treatment of amyloid formation, deposition, accumulation and/or persistence in Alzheimer's disease, type II diabetes and other amyloidoses.

Yet another object of the present invention is to use the polyphenols contained within *Uncaria tomentosa* for the treatment of amyloid formation, deposition, accumulation and/or persistence in Alzheimer's disease, type II diabetes and other amyloidoses.

Yet another object of the present invention is to use the triterpines contained within *Uncaria tomentosa* for the treatment of amyloid formation, deposition, accumulation and/or persistence in Alzheimer's disease, type II diabetes and other amyloidoses.

Yet another object of the present invention is to use the plant sterols, beta-sitosterol, stigmasterol and campesterol contained within *Uncaria tomentosa* for the treatment of amyloid formation, deposition, accumulation and/or persistence in Alzheimer's disease, type II diabetes and other amyloidoses.

Yet another object of the present invention is to use the phytosterols contained within *Uncaria tomentosa* for the treatment of amyloid formation, deposition, accumulation and/or persistence in Alzheimer's disease, type II diabetes and other amyloidoses.

Yet another object of the present invention is to use one or more of the phytochemicals contained within *Uncaria tomentosa*, or its constituent compounds, for the treatment of amyloid formation, deposition, accumulation and/or persistence in Alzheimer's disease, type II diabetes and other amyloidoses. These constituents are believed to include, but not be limited to, 3-beta, 6beta, 19-alpha-trihydroxy-urs-12-en-28-oic-acid, 5-alpha-carboxystrictosidine, Alloisopteropodine, Allopteropodine, Angustine, Dihydrocorynantheine, Dihydrocorynantheine-n-oxide, Hirsutine, Hirsutine-n-oxide, Isomitraphylline, Isopteropodine, Isorhynchophylline, Isorhynchophylline-n-oxide, Isorotundifoline, Mitraphylline, Oleanolic-acid, Pteropodine, Quinovic-acid-3beta-o-(Beta-d-glucopyranosyl-(1→3)beta-d-fucopyranosyl-(27→1) beta d-glucopyranosyl-ester, Quinovic-acid-3beta-o-beta-d-fucopyranoside, Quinovic-acid-3beta-o-beta-d-fucopyranosyl-(27→1)beta-d-glucopyranosylester, Quinovic-acid-3beta-o-beta-d-quinovopyranoside, Rhynchophylline, Rotundifoline, Speciophylline, Uncarine, Uncarine-f, and Ursolic acid.

Yet another object of the present invention is to use other known phytochemicals previously identified by Keplinger as possibly useful for stimulating the human immune system. These include alkaloid, phenol, quinone and terpene based compounds disclosed in U.S. Pat. No. 4,844,901 and U.S. Pat. No. 4,940,725 by Keplinger et al, the texts of which are hereby incorporated by reference, and include, but are not limited to, tetra- and pentacyclic oxindole alkaloids, alkaloids such as alloisopteropodine, isomer A having the formula $C_{21}H_{24}O_4N_2$, allo-pteropodine, isomer B having the formula $C_{21}H_{24}O_4N_2$, normal-isomitraphylline, isomer A having the formula $C_{21}H_{24}O_4N_2$, normal-isorhychophylline, isomer A having the formula $C_{22}H_{28}O_4N_2$, normal-mitraphylline, isomer B having the formula $C_{21}H_{24}O_4N_2$, normal-rhynchophyllin isomer B having the formula $C_{22}H_{28}O_4N_2$, and the oxindole alkaloid speciophylline, Cepharanthine (bisbenzylisochinoline alkaloid), Berbamine (bisbenzylisochinoline alkaloid), Matrine (lupine alkaloid), Pilocarpine (imidazole alkaloid), phenols and quinones such as 2,3-Dihydroxybenzoic acid, Ferulic acid, Anethole, Cleistanthine (lignane), Curculigoside and Curculigoside B (phenolglucosides), Urunshiole (pyrocatechin derivatives with $C_{15}/C_{17}$ side chains, alpha-Tocopherole (vitamin E), Ubichone (mainly Q7, Q8), Maesanine (chinone with $C_{15}$-side-chain), terpenes such as Zexbrevine A/B (sesquiterpenelacetone of the ceramacrane type), 12-O-Tetradeoanoyl-phorbol-13-acetate, TPA (tetracyclic diterpene), Saponine with aglycone oleonic acid (pentacyclic triterpene), and Cynonchoside (steroidglycoside).

Yet another object of the present invention is to provide methods to isolate the active ingredients present within *Uncaria tomentosa* for use as potent agents which inhibit amyloid formation, amyloid deposition, amyloid accumulation, amyloid persistence, amyloid protein-amyloid protein interactions, and/or cause a dissolution/disruption of pre-formed or pre-deposited amyloid fibrils in Alzheimer's disease, type II diabetes and other amyloidoses. Methods for isolation of the active ingredients within *Uncaria tomentosa* include application of some standard techniques known to those skilled in the art, including, but not limited to, thin layer chromatography using silica-coated plates, and separation and isolation using high pressure liquid chromatography (HPLC). Unknown active ingredients within Uncaria tomentosa found to be potent inhibitors of amyloid formation, amyloid deposition, amyloid accumulation, amyloid persistence, amyloid protein-amyloid protein interactions, and/or cause a dissolution/disruption of pre-formed or pre-deposited amyloid fibrils in Alzheimer's disease, type II diabetes and other amyloidoses, are identified by re-testing of individual bands or fractions (separated by thin layer chromatography, column chromatography and/or HPLC) using specific assay tests as described in the examples of the present invention. Sufficient isolation of these active ingredients contained within individual bands and/or fractions are then sent out for specific analyses which may include, but are not limited to, scanning electron microscope equipped with energy dispersive x-ray analyzer to detect and spatially map some elements present in each sample, elemental analysis by combustion to determine the relative % of carbon, hydrogen and nitrogen, high resolution mass spectroscopy to determine molecular weight and elemental composition, fourier transform infrared spectroscopy to determine functional groups and make comparisons to the spectra of known compounds, differential scanning calorimetry to determine melting point, atomic absorption, gel chromatography, high performance liquid chromatography, proton and $C^{13}$ nuclear magnetic resonance spectroscopy for material characterization and to provide information regarding the position of atoms relative to each other, and UV/VIS spectroscopy. It is expected that additional techniques will be developed as part of the further isolation of potent active ingredients within *Uncaria tomentosa*.

Yet another object of the present invention is to provide the use of *Uncaria tomentosa* and/or its ingredients [(regardless of commercial source and regardless of final form for consumption by humans, i.e. pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, bark bundles and/or bark powder ] for inhibition of amyloid formation, deposition, accumulation, and/or persistence, regardless of its clinical setting.

Yet another object of the present invention is to provide compositions and methods involving administering to a subject a therapeutic dose of *Uncaria tomentosa* (or its active ingredients) which inhibits amyloid deposition. Accordingly, the compositions and methods of the invention are useful for inhibiting amyloidosis in disorders in which amyloid deposition occurs. The compounds of the invention can be used therapeutically to treat amyloidosis or can be used prophylactically in a subject susceptible to amyloidosis. The methods of the invention are based, at least in part, in directly inhibiting amyloid fibril formation, inhibiting amyloid fibril growth, and/or causing dissolution/disruption of preformed amyloid fibrils.

Yet another object of the present invention is to provide pharmaceutical compositions for treating amyloidosis. The pharmaceutical compositions include a therapeutic compound of the invention in an amount effective to inhibit amyloid deposition and a pharmaceutically acceptable vehicle.

Yet another object of the present invention is the use of any and all synthetic compounds made that are functionally similar to *Uncaria tomentosa* in therapeutic application, and/or *Uncaria tomentosa's* amyloid inhibitory ingredients, for use as agents to inhibit amyloid formation, amyloid deposition, amyloid accumulation, amyloid persistence, amyloid protein-amyloid protein interactions, and/or cause a dissolution/ disruption of pre-formed or pre-deposited amyloid fibrils in Alzheimer's disease, type II diabetes and other amyloidoses.

Another object of the present invention is to use the inner bark and/or roots from *Uncaria tomentosa* for promoting mental alertness and for inhibiting the formation of brain amyloid deposits in a human subject.

Yet another object of the present invention is to use the inner bark and/or roots from *Uncaria tomentosa* for mental acuity; to promote mental alertness; to provide nutritional support for age or related cognitive or memory decline; to promote cognitive well being; to support brain function; to improve cognitive ability, mental performance or memory; to promote concentration and mental sharpness; to improve mental vitality; to promote greater mental clarity and alertness; to improve short term memory, for age associated cognitive or memory decline; to support normal brain function; to enhance learning or memory; to improve concentration; to enhance mental performance; to reduce mental decline; to reduce likelihood of age related brain disorders; to maintain good brain health; to reduce, eliminate, prevent, inhibit or disrupt/dissolve amyloid fibril or protein deposits, brain associated amyloid fibril deposits or brain associated amyloid protein deposits, amyloid fibril formation and growth or age associated amyloid fibril formation and growth, brain associated amyloid fibril formation and growth, interaction of amyloid protein with glycosaminoglycans, or with proteoglycans; to support healthy pancreatic function; to promote pancreatic function by helping to promote normal insulin function; to reduce, eliminate, prevent, inhibit or disrupt/dissolve amyloid fibril or protein deposits, pancreas associated amyloid fibril or protein deposits, amyloid fibril formation and growth, pancreas associated amyloid fibril formation and growth, and interaction of amyloid protein with glycosaminoglycans or with proteoglycans.

It is yet another object of the invention to meet any or all of the needs summarized above.

These and such other objects of the invention as will become evident from the disclosure below are met by the invention disclosed herein.

Application of the invention to these needs is especially beneficial in that the invention is the only system that effectively provides for use of extracts from the inner bark and root parts of *Uncaria tomentosa*, and use of the ingredients contained within the various commercial preparations of *Uncaria tomentosa*, to benefit human patients with Alzheimer's disease and other amyloidoses due to *Uncaria tomentosa's* newly discovered ability to inhibit amyloid fibril formation, inhibit amyloid fibril growth, inhibit amyloid-proteoglycan interactions, amyloid-glycosaminoglycan interactions, and cause dissolution and/or disruption of preformed amyloid fibrils.

The present invention pertains to the identification and surprising discovery that the inner bark and root parts of *Uncaria tomentosa*, otherwise known as Uña de Gato (or Cat's claw), act as an inhibitor of Alzheimer's disease amyloid formation and growth. In addition, *Uncaria tomentosa* also has the ability to inhibit amyloid protein-proteoglycan (PG)/glycosaminoglycan (GAG) interactions, which are believed to be important for the formation and persistence of all amyloid deposits in tissues. Furthermore, *Uncaria tomentosa* has the ability to dissolve/disrupt pre-formed amyloid fibrils of the Alzheimer's and type II diabetes types, suggesting that this agent may be useful for patients at latter stages of both Alzheimer's disease, type II diabetes and other amyloidoses. *Uncaria tomentosa* extracted from different commercial sources (extracts isolated from gelatin-coated capsules, caplets or liquid form) were all found to serve as potent inhibitors of Alzheimer's disease amyloid fibrillogenesis.

While results are exemplified with Species *tomentosa*, other species of Uncaria are believed to have similar effect.

Commercially available glucosamine (hydrochloride salt, or the sulfate salt), which contained *Uncaria tomentosa* caused a marked significant inhibition of A$\beta$ amyloid fibril formation as determined using a Thioflavin T fluorometry assay. This inhibitory effect was attributed to the presence of *Uncaria tomentosa* (and not due to the presence of glucosamine hydrochloride salt or to the glucosamine sulfate salt), as pure *Uncaria tomentosa* (but not pure glucosamine hydrochloride salt or glucosamine sulfate salt) derived from different commercial sources were potent inhibitors of amyloid fibril formation. *Uncaria tomentosa* (without other additives) obtained from different commercial sources inhibited A$\beta$ amyloid fibrillogenesis in a dose-dependent manner. *Uncaria tomentosa* also inhibited Alzheimer's A$\beta$—A$\beta$ interactions as determined using a solid phase binding assay demonstrating that *Uncaria tomentosa* is additionally an effective inhibitor of Alzheimer's amyloid fibril growth. Furthermore, *Uncaria tomentosa* was effective in the dose-dependent inhibition of A$\beta$-proteoglycan/glycosaminoglycan (PG/GAG) interactions (an important therapeutic target for all amyloidoses) as determined using a solid phase binding immunoassay. *Uncaria tomentosa* derived from different commercial sources was also a potent dissolving/inhibiting agent of pre-formed A$\beta$ (1–40) or A$\beta$ (1–42) containing amyloid fibrils, as determined using Thioflavin T fluorometry and Congo red staining assays. This latter effect occurred in a dose-dependent manner, causing a significant ($p<0.001$) 70% dissolution within a 2 hour incubation period. In addition, *Uncaria tomentosa* was a potent dissolving agent of islet amyloid fibrils (ie. amylin), causing a 72% dissolution within a 2 hour incubation period, and a 80% dissolution by 4 days. *Uncaria tomentosa* which was effective in all of the studies described above were all derived from *Uncaria tomentosa* extract obtained from pill, tablet or liquid form, and were all currently available commercially for oral use in humans. Therefore, the present invention claims the use of *Uncaria tomentosa* (in a pill, tablet or liquid form) and derivatives thereof from different commercial sources for the treatment of amyloidosis in Alzheimer's disease, type II diabetes and other amyloidoses. Also disclosed are methods of isolation to identify and purify the key amyloid inhibitory ingredients within the plant material. Identification of the "active" amyloid inhibitory ingredients within the extracted plant materials are anticipated to lead to new drug design for anti-amyloid therapeutics of the future. Current use of *Uncaria tomentosa* and its ingredients contained within different commercial preparations are anticipated to benefit human patients at all stages of Alzheimer's disease due to *Uncaria tomentosa's* inherent ability to inhibit Aβ amyloid fibril formation (early to mid-stage Alzheimer's disease), inhibit amyloid fibril growth (early to mid-stage Alzheimer's disease), inhibit amyloid-PG/GAG interactions (all stages of Alzheimer's disease) and cause dissolution/disruption of preformed amyloid fibrils (mid to late stages of Alzheimer's disease). Similarly, *Uncaria tomentosa* is anticipated to benefit patients with different systemic amyloid diseases such as type II diabetes, regardless of the stage of amyloid accumulation and the organ (or tissue) involved.

In another particular aspect of the invention there is a method of isolation to purify and identify the amyloid inhibitory ingredients from *Uncaria tomentosa* and/or extracts thereof. In one such method, an extract prepared from commercially obtained pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, bark bundles and/or bark powder, using the method employing some or all of the following steps:

a) extraction from *Uncaria tomentosa* regardless of form as described above using an organic solvent such as propanol, b) concentration of the extract by using a method such as rotary evaporation, lyophilization or precipitation, c) centrifugation of the extract to remove insoluble materials, d) recentrifugation of the supernatant to further remove insoluble material, e) precipitation of the active ingredients using an organic solvent such as petroleum ether followed by centrifugation, f) re-dissolving the pellet obtained in an organic solvent such as propanol, g) applying to a silica column equilibrated with propanol/10% acetic acid and eluting with the same solvent, h) collecting the fastest-moving fraction (orange/brown-yellow colored fractions) as determined by sight or by monitoring at 490 nm, i) precipitation of the active components using an organic solvent such as petroleum ether, followed by centrifugation, j) re-dissolving the pellet obtained in acetonitrile/water/acetic acid, and k) injecting and separation by HPLC, l) identifying amyloid inhibitory ingredients by testing in relevant in vitro and in vivo assays, and m) sending out for structural analysis and elemental composition, as described herein.

These and other features and advantages of the present invention will become more fully apparent when the following detailed description of the invention is read in conjunction with the accompanying figures.

In other aspects of the invention, a pharmaceutical agent is disclosed for treating an amyloid disease in a patient, wherein the pharmacological agent comprises a therapeutically effective amount of plant matter from a plant of the genus Uncaria. The pharmacological agent is preferably from a plant of the genus *Uncaria*, species *tomentosa*. The pharmacological agent is preferably an extract obtained from *Uncaria tomentosa*, the extract being derived from the inner bark or root tissue of *Uncaria tomentosa*, and advantageously taken from some commercially available source, such as pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, bark bundles or bark powder.

In preferred embodiments, the pharmacological agent is an amyloid inhibitory ingredient selected from the group consisting of oxindole alkaloids, quinovic acid glycosides, proanthocyanidins, polyphenols, triterpines, plants sterols, beta-sitosterol, stigmasterol, campesterol, phytosterols, 3-beta, 6beta, 19alpha-trihydroxy-urs- 12-en-28-oic-acid, 5alpha-carboxystrictosidine, alloisopteropodine, allopteropodine, angustine, dihydrocorynantheine, dihydrocorynantheine-n-oxide, hirsutine, hirsutine-n-oxide, isomitraphylline, isopteropodine, isorhynchophylline, isorhynchophylline-n-oxide, isorotundifoline, curculogoside, curculigoside B, phenolglucosides, 2-[[2,6-dimethoxybenzoyl)oxy]methyl-4-hydroxyphenyl-beta-D-glucopyranoside, 2-[[2-hydroxy-6-methoxybenzoly)oxy]methyl-4-hydroxyphenyl-beta-D-glucopyranoside, mitraphylline, oleanolic-acid, pteropodine, quinovic-acid-3beta-o-(Beta-dglucopyranosyl-(1→3)beta-d-fucopyranosyl-(27→1)-beta-d-glucopyranosyl-ester quinovic-acid-3beta-o-beta-d-fucopyranoside, quinovic-acid-3beta-o-beta-d-fucopyranosyl-(27→1)-beta-d-glucopyranosylester, quinovic-acid-3beta-o-beta-d-quinovopyranoside, rhynchophylline, rotundifoline, speciophylline, uncarine, uncarine-f, ursolic acid, cepharanthine (bisbenzylisochinoline alkaloid), berbamine (bisbenzylisochinoline alkaloid), matrine (lupine alkaloid), pilocarpine (imidazole alkaloid), 2,3-Dihydroxybenzoic acid, ferulic acid, anethole, cleistanthine (lignane), phenolglucosides, urunshiole, alpha-tocopherole (vitamin E), ubichone, maesanine, zexbrevine A/B, 12-O-tetradeoanoyl-phorbol-13-acetate, TPA (tetracyclic diterpene), saponine with aglycone oleonic acid (pentacyclic triterpene), and cynonchoside.

The pharmacological agent preferably has a therapeutically effective amount of *Uncaria tomentosa* in a dosage in the range of from about 10 to 1,000 mg/kg of body weight of the patient, and more preferably in the range of from about 10 to 100 mg/kg of body weight of the patient.

The amyloid disease for treatment with the pharmacological agent is selected from the group consisting of the amyloid associated with Alzheimer's disease, Down's syndrome and hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

Preferred pharmaceutical agents have a weight percentage of plant extract in the agent is in the range of from about 70% to about 95%, and may also have a pharmaceutically acceptable carrier, diluent or excipient. The pharmaceutical agent preferably has an amyloid inhibitory activity or efficacy greater than 50%.

In addition, *Uncaria tomentosa* has the ability to inhibit the formation of brain amyloid deposits in patients who accumulate brain amyloid deposits that occur during normal aging and in a variety of brain disorders including Alzheimer's Disease; it will therefore promote mental alertness in such patients.

*Uncaria tomentosa* also has the ability to reduce, eliminate, prevent, inhibit or disrupt/dissolve amyloid fibril or protein deposits, brain associated amyloid fibril deposits or brain associated amyloid protein deposits, as well as amyloid fibril formation and growth or age associated amyloid fibril formation and growth, brain associated amyloid fibril formation and growth, and interaction of amyloidprotein with glycosaminoglycans, or with proteoglycans; it will therefore promote mental acuity, promote mental alertness, provide nutritional support for age or related cognitive or memory decline, promote cognitive well being, support brain function, improve cognitive ability, mental performance or memory, promote concentration and mental sharpness, improve mental vitality, promote greater mental clarity and alertness, improve short term memory, reduce or reverse age associated cognitive or memory decline, support normal brain function, enhance learning or memory; improve concentration, enhance mental performance, reduce mental decline, reduce likelihood of age related brain disorders, and maintain good brain health.

*Uncaria tomentosa* further has the ability to reduce, eliminate, prevent, inhibit or disrupt/dissolve amyloid fibril or protein deposits, pancreas associated amyloid fibril or protein deposits, as well as amyloid fibril formation and growth, pancreas associated amyloid fibril formation and growth, and interaction of amyloid protein with glycosaminoglycans or with proteoglycans; it will therefore support healthy pancreatic function and promote pancreatic function by helping to promote normal insulin function.

Another aspect of the invention is a method for isolating amyloid inhibitory constituents within *Uncaria tomentosa* plant matter, the method comprising the following steps: a) extracting the plant matter with an organic solvent, b) concentrating the extract, c) removing insoluble materials, d) precipitating amyloid inhibitory constituents with organic solvent e) recovering and redissolving the amyloid inhibitory constituents obtained in organic solvent, and f) injecting and separation by HPLC.

The plant matter is preferably comprised of commercially obtained pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, bark bundles and/or bark powder, which contain *Uncaria tomentosa*, extracts or derivatives thereof, and may be taken from commercially available gelatin-coated capsules which contain dried-powder of *Uncaria tomentosa*, extracts or derivatives thereof.

The step of extracting the plant matter with an organic solvent further comprises adding propanol initially to plant materials that are powdered, and the resulting mixture is stirred overnight. The solvent used in the step of extracting amyloid inhibitory ingredients preferably has a polarity ranging from that of water to that of pentanol. The step of removing insoluble materials is preferably effected by centrifuging the extract and collecting the supernatant. The step of concentrating the extract is preferably effected by rotary evaporation. Following the extraction and centrifugation steps, the extraction and centrifugation procedure is preferably repeated 1–5 more times and the supernatants are collected.

Following the repeated steps of extraction and concentration, the supernatants are preferably pooled and concentrated using a rotary evaporator. Following the concentrating step, and after the volume is about 500 mls or less, the extract is preferably recentrifuged to further remove insoluble materials. Following the recentrifugation step, the supernatant is preferably obtained and precipitated with petroleum ether, preferably 4 volumes. Following precipitation with petroleum ether, the precipitate is preferably collected in a pellet following further centrifugation. The pellet is then preferably dissolved in propanol and applied to a silica column equilibrated with propanol containing acetic acid. Following the application of the material to a silica column, propanol containing acetic acid is used to elute, and the fastest moving yellowish-brown colored fractions are collected with a fraction collector. The eluents from the column are preferably monitored spectroscopically at 490 nm and fractions are collected in a fraction collector. Following collection of the fastest moving yellowish-brown colored fractions, the fractions are precipitated with petroleum ether, and the precipitate is collected following centrifugation. Following reprecipitation and recentrifugation, the pellet is dissolved in acetonitrile/acetic acid/water for high pressure liquid chromatography (HPLC) injection. The dissolved pellet is divided into equal portions and injected into an HPLC. The HPLC used preferably contains a 1×25 cm $C_{18}$ column, though other sizes may be made to serve, and is maintained at 30° C. with a flow rate of 2 ml/min. The sample portions injected onto the HPLC are eluted with gradients of A and B, such that 0% B for 5 minutes, 0–15% B from 5–10 minutes, 15–45% B from 10–70 minutes, and 45–100% B from 70–85 minutes; where B=95% acetonitrile with 0.5% acetic acid in distilled water and A=5% acetonitrile with 0.5% acetic acid in distilled water. The eluents from the HPLC are monitored at 490 nm and 4 ml fractions are collected in a fraction collector and pooled peaks are obtained at various retention times (from 0 through 85 minutes). The fractions obtained may be concentrated by lyophilization after most of the acetonitrile is removed by rotary evaporation.

The concentrated fractions obtained are then tested in relevant in vitro assays to identify potent inhibitors of amyloid fibril formation, amyloid fibril growth or dissolution/disruption of pre-formed amyloid fibrils. The amyloid inhibitory ingredients within *Uncaria tomentosa* are preferably drawn from the HPLC approximate HPLC retention times of 13–45 minutes, and more preferably 26 minutes.

A method is also disclosed for treating an amyloid disease in a patient, comprising the step of administering to the patient a therapeutically effective amount of plant matter from a plant of the genus *Uncaria*, species *tomentosa*. The plant matter is preferably administered orally or by aerosol spray or in a parenterally injectable or infusible form.

The therapeutically effective amount of plant matter is preferably an amyloid inhibitory ingredient selected from the group consisting of oxindole alkaloids, quinovic acid glycosides, proanthocyanidins, polyphenols, triterpines, plants sterols, beta-sitosterol, stigmasterol, campesterol, phytosterols, 3-beta, 6beta, 19alpha-trihydroxy-urs- 12-en-28-oic-acid, 5alpha-carboxystrictosidine, alloisopteropodine, allopteropodine, angustine, dihydrocorynantheine, dihydrocorynantheine-n-oxide, hirsutine, hirsutine-n-oxide, isomitraphylline, isopteropodine, isorhynchophylline, isorhynchophylline-n-oxide, isorotundifoline, curculogoside, curculigoside B, phenolglucosides, 2-[[2,6-dimethoxybenzoyl)oxy]methyl-4-hydroxyphenyl-beta-D-glucopyranoside, 2-[[2 hydroxy-6-methoxbenzoly)oxy]methyl-4-hydroxyphel-beta-D- glucopyranoside, mitraphylline, oleanolic-acid, pteropodine, quinovic-acid-3beta-o-(Beta-dglucopyranosyl-(1→3)beta-d-fucopyranosyl-(27→1)-beta-d-glucopyranosyl-ester quinovic-acid-3beta-o-beta-d-fucopyranoside, quinovic-acid-3beta-o-beta-d-fucopyranosyl-(27→1)-beta-d-glucopyranosylester, quinovic-acid-3beta-o-beta-d-quinovopyranoside, rhynchophylline, rotundifoline, speciophylline, uncarine, uncarine-f, ursolic acid, cepharanthine (bisbenzylisochinoline alkaloid), berbamine (bisbenzylisochinoline alkaloid), matrine (lupine alkaloid), pilocarpine (imidazole alkaloid), 2,3-Dihydroxybenzoic acid, ferulic acid, anethole, cleistanthine (lignane), phenolglucosides, urunshiole, alpha-tocopherole (vitamin E), ubichone, maesanine, zexbrevine A/B, 12-O-tetradeoanoyl-phorbol-13-acetate, TPA (tetracyclic diterpene), saponine with aglycone oleonic acid (pentacyclic triterpene), and cynonchoside.

BRIEF DESCRIPTION OF THE DRAWINGS

FIG. 10 are black and white graphs demonstrating separation of *Uncaria tomentosa* extract by high pressure liquid chromatography (HPLC) and initial purification of amyloid inhibitory ingredients. Panel A represents HPLC monitored at 490 nm and eluted with a acetonitrile/water gradient, demonstrating that the *Uncaria tomentosa* extract contained multiple ingredients that eluted off the column, with a broad peak observed at 13–45 minutes, and a peak observed at 80 minutes. Panel B demonstrates a fraction at 26 minutes that was re-injected and a symmetrical peak was obtained indicating that the polydispersity of the panel A chromatogram is not due to column artifact, but due to the presence of individual components within the *Uncaria tomentosa* extract. In Panel C, 60 μl of 25 μM of pre-fibrillized Aβ 1–40 was incubated for 2 hours in the presence or absence of 0.0005 OD units of fraction 26 and fraction 80. Fraction 26 (but not fraction 80) exhibited potent amyloid inhibitory activity causing an 85% dissolution/disruption of Alzheimer's disease amyloid within a 2-hour incubation period.

BEST MODE OF CARRYING OUT THE INVENTION

Figure 1:
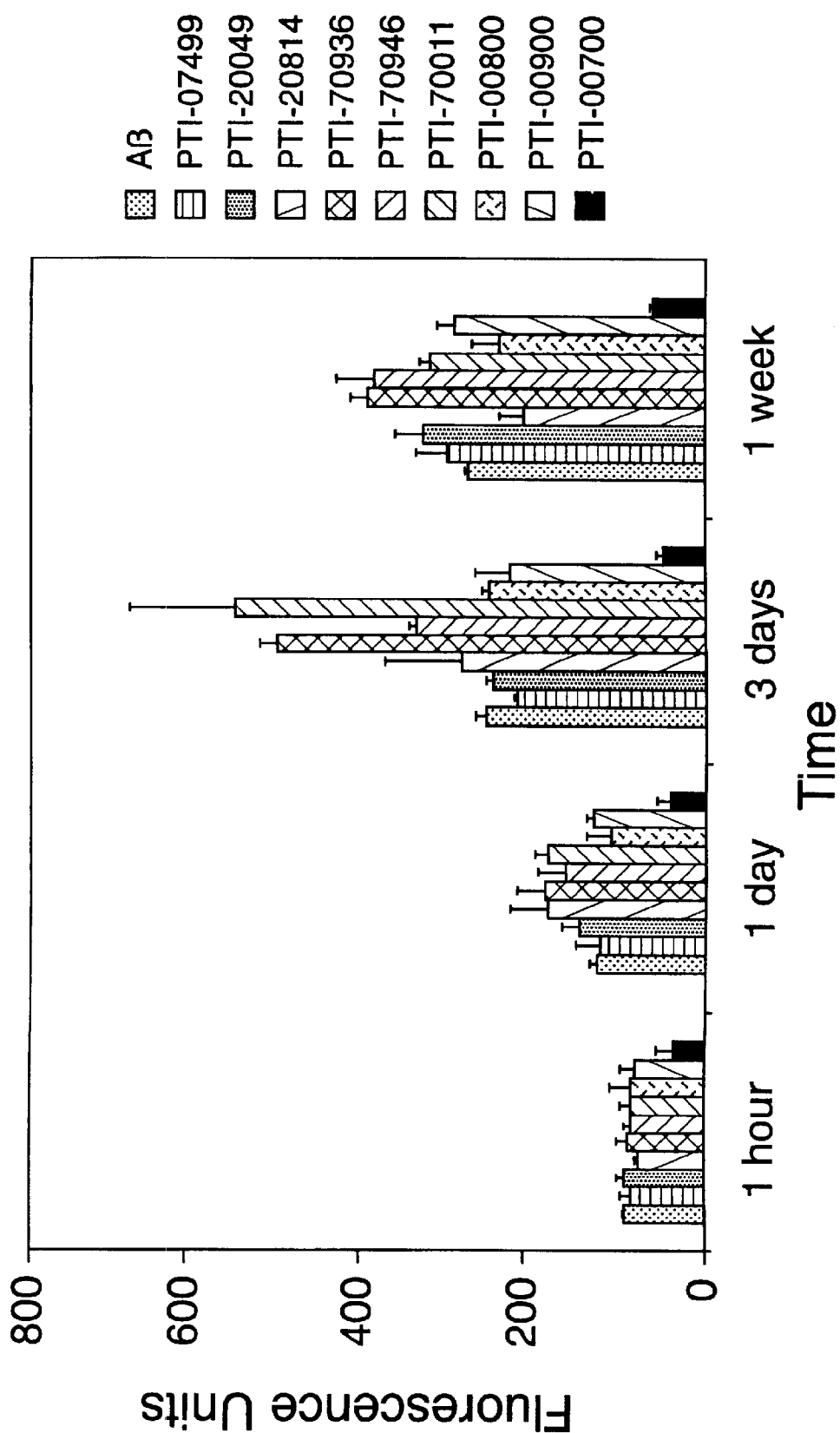
FIG. 1 is a black and white graph of a 1 week Thioflavin T fluorometry assay utilized to identify inhibitors of Alzheimer's Aβ (1–40) amyloid fibril formation. Glucosamine (sulfate salt) containing *Uncaria tomentosa* (PTI-00700) is shown to be a potent inhibitor of Aβ (1–40) amyloid fibril formation.

Turning now to the drawings, the invention will be described in a preferred embodiment by reference to the numerals of the drawing figures wherein like numbers indicate like parts.

Amyloid and Amyloidosis

Amyloid is a generic term referring to a group of diverse, but specific extracellular protein deposits which all have common morphological properties, staining characteristics, and x-ray diffraction spectra. Regardless of the nature of the amyloid protein deposited all amyloids have the following characteristics: 1) an amorphous appearance at the light microscopic level and appear eosinophilic using hematoxylin and eosin stains; 2) all stain with Congo red and demonstrate a red/green birefringence as viewed under polarized light (Puchtler et al., *J. Histochem. Cytochem.* 10:355–364, 1962), 3) all contain a predominant beta-pleated sheet secondary structure, and 4) ultrastructurally amyloid usually consist of non-branching fibrils of indefinite length and with a diameter of 7–10 nm.

Amyloid today is classified according to the specific amyloid protein deposited. The amyloid diseases include, but are not limited to, the amyloid associated with Alzheimer's disease, Down's syndrome and Hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as $beta_2$-microglobulin amyloid), the amyloid associated with senile cardiac amyloid and Familial Amyloidotic Polyneuropathy (wherein the specific amyloid is referred to as prealbumin or transthyretin amyloid), and the amyloid associated with endocrine tumors such as medullary carcinoma of the thyroid (wherein the specific amyloid is referred to as variants of procalcitonin).

Although amyloid deposits in clinical conditions share common physical properties relating to the presence of a beta-pleated sheet conformation, it is now clear that many different chemical types exist and additional ones are likely to be described in the future. It is currently thought that there are several common pathogenetic mechanisms that may be operating in amyloidosis in general. In many cases, a circulating precursor protein may result from overproduction of either intact or aberrant molecules (ex. plasma cell dyscrasias), reduced degradation or excretion (serum amyloid A in some secondary amyloid syndromes and $beta_2$-microglobulin in long-term hemodialysis), or genetic abnormalities associated with variant proteins (ex. familial amyloidotic polyneuropathy). Proteolysis of a larger protein precursor molecule occurs in many types of amyloidosis, resulting in the production of lower molecular weight fragments that polymerize and assume a beta-pleated sheet conformation as tissue deposits, usually in an extracellular location. What are the precise mechanisms involved, and the aberrant causes leading to changes in proteolytic processing and/or translational modifications is not known in most amyloids.

Systemic amyloids which include the amyloid associated with chronic inflammation, various forms of malignancy and Familial Mediterranean Fever (ie. AA amyloid or inflammation-associated amyloidosis)(Benson and Cohen, *Arth. Rheum.* 22:36–42, 1979; Kamei et al, *Acta Path. Jpn.* 32:123–133, 1982; McAdam et al, *Lancet* 2:572–573, 1975; Metaxas, *Kidney Int.* 20:676–685, 1981), and the amyloid associated with multiple myeloma and other B-cell dyscrasias (ie. AL amyloid)(Harada et al, *J. Histochem. Cytochem.* 19:1–15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, *N. Engl. J. Med.* 321:513–518, 1989). For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3–5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (amylin) deposits found in the islets of Langerhans in the pancreas of 90% of patients with type II diabetes (Johnson et al, *N. Engl. J. Med.* 321:513–518, 1989; *Lab. Invest.* 66:522–535, 1992); the $beta_2$-microglobulin amyloid deposits in the medial nerve leading to carpal tunnel syndrome as observed in patients undergoing long-term hemodialysis (Geyjo et al, *Biochem. Biophys. Res. Comm.* 129:701–706, 1985; *Kidney Int.* 30:385–390, 1986); the prealbumin/transthyretin amyloid observed in the hearts of patients with senile cardiac amyloid; and the prealbumin/transthyretin amyloid observed in peripheral nerves of patients who have Familial Amyloidotic Polyneuropathy (Skinner and Cohen, *Biochem. Biophys. Res. Comm.* 99:1326–1332, 1981; Saraiva et al, *J. Lab. Clin. Med.* 102:590–603, 1983; *J. Clin. Invest.* 74:104–119, 1984; Tawara et al, *J. Lab. Clin. Med.* 98:811–822, 1989). *Alzheimer's Disease and the Aging Population.*

Alzheimer's disease is a leading cause of dementia in the elderly, affecting 5–10% of the population over the age of 65 years (*A Guide to Understanding Alzheimer's Disease and Related Disorders*, edited by Jorm, New York University Press, New York, 1987). In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's on ward. Alzheimer's disease today affects 4–5 million Americans, with slightly more than half of these people receiving care at home, while the others are in many different health care institutions. The prevalence of Alzheimer's disease and other dementias doubles every 5 years beyond the age of 65, and recent studies indicate that nearly 50% of all people age 85 and older have symptoms of Alzheimer's disease (1997 *Progress Report on Alzheimer's Disease.* National Institute on Aging/National Institute of Health). 13% (33 million people) of the total population of the United States are age 65 and older, and this % will climb to 20% by the year 2025 (1997 *Progress Report on Alzheimer's Disease*, National Institute on Aging/National Institute of Health).

Alzheimer's disease also puts a heavy economic burden on society as well. A recent study estimated that the cost of caring for one Alzheimer's disease patient with severe cognitive impairments at home or in a nursing home, is more than $47,000 per year (*A Guide to Understanding Alzheimer's Disease and Related Disorders.* edited by Jorm, New York University Press, New York, 1987). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (1997 *Progress Report on Alzheimer's Disease*, National Institute on Aging/National Institute of Health).

Tacrine hydrochloride ("Cognex"), the first FDA approved drug for Alzheimer's disease is a acetylcholinesterase inhibitor (Cutler and Sramek, *N. Engl. J. Med.*

328:808–810, 1993). However, this drug has showed limited success in the cognitive improvement in Alzheimer's disease patients and initially had major side effects such as liver toxicity. The second more recently FDA approved drug, donepezil (also known as "Aricept"), which is also an acetylcholinesterase inhibitor, is more effective than tacrine, by demonstrating slight cognitive improvement in Alzheimer's disease patients (Barner and Gray, *Ann. Pharmacotherapy* 32:70–77, 1998; Rogers and Friedhoff, *Eur. Neuropsych.* 8:67–75, 1998), but is not believed to be a cure. Therefore, it is clear that there is a need for more effective treatments for Alzheimer's disease patients. *Amyloid as a Therapeutic Target for Alzheimer's Disease*

Alzheimer's disease is characterized by the deposition and accumulation of a 39–43 amino acid peptide termed the beta-amyloid protein, Aβ or β/A4 (Glenner and Wong, *Biochem. Biophys. Res. Comm.* 120:885–890, 1984; Masters et al, *Proc. Natl. Acad. Sci. USA* 82:4245–4249, 1985; Husby et al, *Bull WHO* 71:105–108, 1993). Aβ is derived from larger precursor proteins termed beta-amyloid precursor proteins (or βPPs) of which there are several alternatively spliced variants. The most abundant forms of the βPPs include proteins consisting of 695, 751 and 770 amino acids (Tanzi et al, *Nature* 331:528–530, 1988; Kitaguchi et al, *Nature* 331:530–532, 1988; Ponte et al, *Nature* 331:525–527, 1988).

The small Aβ peptide is a major component which makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science* 251:675–678, 1991). The pathological hallmarks of Alzheimer's disease is therefore the presence of "plaques" and "tangles", with amyloid being deposited in the central core of plaques. The other major type of lesion found in the Alzheimer's disease brain is the accumulation of amyloid in the walls of blood vessels, both within the brain parenchyma and in the walls of meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79–90, 1986; Pardridge et al, *J. Neurochem.* 49:1394–1401, 1987).

For many years there has been an ongoing scientific debate as to the importance of "amyloid" in Alzheimer's disease and whether the "plaques" and "tangles" characteristic of this disease, were a cause or merely the consequences of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al, *Br. Res.* 563:311–314, 1991; *J. Neurochem.* 64:253–265, 1995). Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus (Harrigan et al, *Neurobiol.Aging* 16:779–789, 1995) and induces nerve cell death in transgenic mice (Games et al, *Nature* 373:523–527, 1995; Hsiao et al, *Science* 274:99–102, 1996). Injection of the Alzheimer's Aβ into rat brain also causes memory impairment and neuronal dysfunction (Flood et al, *Proc. Natl. Acad. Sci.* 88:3363–3366, 1991; *Br. Res.* 663:271–276, 1994).

Probably, the most convincing evidence that Aβ amyloid is directly involved in the pathogenesis of Alzheimer's disease comes from genetic studies. It has been discovered that the production of Aβ can result from mutations in the gene encoding, its precursor, beta-amyloid precursor protein (Van Broeckhoven et al, *Science* 248:1120–1122, 1990; Murrell et al, *Science* 254:97–99, 1991; Haass et al, *Nature Med.* 1:1291–1296, 1995). The identification of mutations in the beta-amyloid precursor protein gene which causes early onset familial Alzheimer's disease is the strongest argument that amyloid is central to the pathogenetic process underlying this disease. Four reported disease-causing mutations have now been discovered which demonstrate the importance of Aβ in causing familial Alzheimer's disease (reviewed in Hardy, *Nature Genet.* 1:233–234, 1992). All of these studies suggest that providing a drug to reduce, eliminate or prevent fibrillar Aβ formation, deposition, accumulation and/or persistence in the brains of human patients is believed to serve as an effective therapeutic.

*Uncaria tomentosa*

The plant *Uncaria tomentosa*, also known as "Uña de Gato" (in Spanish) or "Cat's claw" (in English) refers to a woody vine which grows within the Peruvian Amazon rain forest. This slow growing vine takes 20 years to reach maturity, and can grow over 100 feet in length as it attaches and wraps itself around the native trees. It is found abundantly in the foothills, at elevations of two to eight thousand feet. The vine is referred to as "Cat's claw" because of its distinctive curved claw-like thorns which project from the base of its leaves. The native Indian tribes traditionally have boiled the inner bark and root of the herb to make a tea decoction and regard *Uncaria tomentosa* as a sacred medicinal plant. The highly effective properties contained within the inner bark of this plant are believed to have a profound and positive influence on the body, although scientific medical data is generally lacking on its potential benefits in humans. The alkaloids and phytochemicals in the inner bark of *Uncaria tomentosa* are almost identical to those found in the root, and harvesting this way preserves the plant and provides for the future of the rainforest.

Some of the active substances present in *Uncaria tomentosa* are alkaloids (see Keplinger patents referred to above), which occur in the plant and its watery extract as a complex bound to tannins. In this form, only little of them can be activated. The complexes get split by the acid milieu of the stomach; the alkaloids get transformed into their hydrochloride form, and in this way, get well absorbed. A darker *Uncaria tomentosa* extract means more tannin is present and beneficial alkaloids are locked up with the tannins, which have formed a non-bioavailable and poorly absorbed complex. A light golden color of *Uncaria tomentosa* suggests that there is less tannins, and more alkaloids available in the extract.

Besides the presence of alkaloids, *Uncaria tomentosa* is believed to also contain other beneficial phytochemicals including quinovic acid glycosides, proanthocyanidins, polyphenols, triterpines and the plant sterols beta-sitosterol, stigmasterol and campesterol (P Steinberg "*Uncaria tomentosa* (Cat's Claw) a wondrous herb from the Peruvian rain forest", *Townsend Letter for Doctors*, May, 1994; P. Steinberg, "Cat's claw update-*Uncaria tomentosa*: that wondrous herb from the Peruvian rain forest", *Townstead Letter for Doctors*, August/September 1995, "Cat's Claw Miracle Herb from the Rain Forest of Peru", Woodland Publ. Inc., Pleasant Grove, Vt., USA).

*Uncaria tomentosa* is one of the most important plants in the South American Peruvian rainforest. A number of oxindole alkaloids have already been isolated from the inner bark of this plant. Two US patents (U.S. Pat. No. 4,844,901 and U.S. Pat. No. 4,940,725 by Keplinger) describe the isolation and use of six oxindole alkaloids from *Uncaria tomentosa*, which are believed to be "suitable for the unspecified stimulation of the immunologic system". These oxindole alkaloids are believed to provide a general boost to the immune system as well as have a profound effect on the ability of white blood cells and macrophages to phagocytize harmful microorganisms and foreign matter. The most immunologically active alkaloid appears to be alloisopteropodine, isomer A, a pentacyclic oxindole alkaloid (U.S. Pat. No. 4,940,725).

Although some health care providers have suggested that *Uncaria tomentosa* may be used to treat a variety of ailments, nowhere has there been any use, or suggestion of use, of this compound for the treatment of amyloid formation, deposition, accumulation and/or persistence, such as that which occurs in the amyloidoses, including Alzheimer's disease. The present invention clearly demonstrates the effectiveness of *Uncaria tomentosa* and its extracts and derivatives obtained from different commercial sources for the 1) inhibition of Alzheimer's Aβ amyloid fibril formation (important for patients in early to mid-stage Alzheimer's disease), 2) inhibition of Alzheimer's amyloid fibril growth (important for patients in early to mid-stage Alzheimer's disease), 3) inhibition of Alzheimer's amyloid-PG/GAG interactions (important for patients in all stages of Alzheimer's disease) and 4) causing the dissolution/disruption of preformed Alzheimer's disease amyloid fibrils. In addition, the present invention demonstrates that *Uncaria tomentosa* is effective in causing the dissolution of islet amyloid fibrils (ie. amylin) and therefore may serve as an effective treatment for ~90% of type II diabetic patients who have islet amyloid accumulation in the pancreas.

The Examples illustrated below all serve well to establish that, at least in vitro, *Uncaria tomentosa* has the ability to inhibit the formation of brain amyloid deposits that occur during normal aging and in a variety of brain disorders including Alzheimer's Disease. In addition, it is known that patients who accumulate brain amyloid deposits eventually lose cognitive ability and memory function and sustain a marked reduction in mental clarity in general. Therefore it follows that inhibition of such brain amyloid deposits will at the least promote mental alertness in such patients.

The Examples also establish that again, at least in vitro, *Uncaria tomentosa* has the ability to reduce, eliminate, prevent, inhibit or disrupt/dissolve amyloid fibril or protein deposits, brain associated amyloid fibril deposits or brain associated amyloid protein deposits, as well as amyloid fibril formation and growth or age associated amyloid fibril formation and growth, brain associated amyloid fibril formation and growth, and interaction of amyloid protein with glycosaminoglycans, or with proteoglycans. In addition, it is known that patients who accumulate amyloid fibril or protein deposits, brain associated amyloid fibril deposits or brain associated amyloid protein deposits, or who display symptoms of amyloid fibril formation and growth or age associated amyloid fibril formation and growth, brain associated amyloid fibril formation and growth, or interaction of amyloid protein with glycosaminoglycans, or with proteoglycans, in general will eventually lose mental acuity, mental alertness, concentration, cognitive well being, or some measure of brain function, or cognitive ability, mental performance or memory, or concentration and mental sharpness, or mental vitality, or mental clarity and alertness, short term memory, or some of the ability to learn or remember. It is also known that such patients are subject to age associated or related cognitive or memory decline, or will sustain a marked reduction in mental clarity. It follows then that inhibition, reduction, elimination, prevention, disruption, or dissolution of such amyloid fibril or protein deposits, brain associated amyloid fibril deposits or brain associated amyloid protein deposits, or amyloid fibril formation and growth or age associated amyloid fibril formation and growth, brain associated amyloid fibril formation and growth, or interaction of amyloid protein with glycosaminoglycans, or with proteoglycans, will improve mental acuity, promote mental alertness, provide nutritional support for age related cognitive or memory decline, promote cognitive well being, support brain function, improve cognitive ability, mental performance or memory, promote concentration and mental sharpness, improve mental vitality, promote greater mental clarity and alertness, improve short term memory, reduce or reverse age associated cognitive or memory decline, support normal brain function, enhance learning or memory; improve concentration, enhance mental performance, reduce mental decline, reduce likelihood of age related brain disorders, and maintain good brain health, in such patients.

The Examples further establish that, at least in vitro, *Uncaria tomentosa* has the ability to reduce, eliminate, prevent, inhibit or disrupt/dissolve amyloid fibril or protein deposits, pancreas associated amyloid fibril or protein deposits, as well as amyloid fibril formation and growth, pancreas associated amyloid fibril formation and growth, and pancreas interaction of amyloid protein with glycosaminoglycans or with proteoglycans. In addition, it is known that patients who accumulate amyloid fibril or protein deposits, pancreas associated amyloid fibril or protein deposits, or who display symptoms of amyloid fibril formation and growth, pancreas associated amyloid fibril formation and growth, or pancreas associated interaction of amyloid protein with glycosaminoglycans or with proteoglycans, in general lose healthy pancreatic function, or sustain a reduction in normal insulin function, leading to loss or reduction of pancreatic function. It therefore follows that inhibition, reduction, elimination, prevention, disruption, or dissolution of such amyloid fibril or protein deposits, pancreas associated amyloid fibril or protein deposits, or amyloid fibril formation and growth, pancreas associated amyloid fibril formation and growth, or pancreas associated interaction of amyloid protein with glycosaminoglycans or with proteoglycans, will support healthy pancreatic function and promote pancreatic function by helping to promote normal insulin function in such patients.

EXAMPLES

The following examples are put forth so as to provide those with ordinary skill in the art with the disclosure and description of the identification and use of commercially available *Uncaria tomentosa* to inhibit amyloid fibril formation, inhibit amyloid fibril growth, inhibit amyloid-PG/GAG interactions, and cause dissolution/disruption of preformed amyloid fibrils. However, it should not be construed that the invention is limited to these specific examples.

Example 1

Glucosamine (Sulfate Salt) Containing *Uncaria tomentosa* is a Potent Inhibitor of Alzheimer's Aβ (–140) Amyloid Fibril Formation A previously described method of measuring amyloid fibril formation utilizing Thioflavin T fluorometry (H Naiki et al, *Lab. Invest.* 65:104–110, 1991; H Levine III, *Protein Sci.* 2:404–410, 1993; H Levine III, *Amyloid: Int. J. Exp. Clin. Invest.* 2:1–6, 1995; H Naiki and K. Nakakuki, *Lab. Invest.* 74:374–383, 1996) was employed initially to identify potential therapeutic compounds capable of inhibiting Alzheimer's Aβ amyloid fibril formation. Using this sensitive assay, any decreases or increases in fluorescence was previously shown to correlate with a decrease or increase in the amount of amyloid fibrils (H Naiki et al, *Lab. Invest.* 65:104–110, 1991; H Levine III, *Protein Sci.* 2:404–410, 1993; H Levine III, *Amyloid: Int. J. Exp. Clin. Invest.* 2:1–6, 1995; H Naiki and K. Nakakuki, *Lab. Invest.* 74:374–383, 1996), allowing one to determine the identification and extent of potential inhibitors and/or enhancers of amyloid fibril formation.

Our screening studies first suggested the detection of a potent Alzheimer's disease amyloid inhibitory agent which was present as an added ingredient in one of the compounds that we initially tested. In one study, the effects of various compounds on Alzheimer's Aβ (1–40) fibril formation was assessed by Thioflavin T fluorometry. Thioflavin T is known to bind to fibrillar amyloid proteins, and an increase in fluorescence correlates with an increase in amyloid fibril formation, whereas a decrease in fluorescence correlates with a decrease in amyloid fibril formation. The Alzheimer's Aβ protein (1–40) when incubated at 37° C. tends to spontaneously form amyloid fibrils which increase in quantity over time. In this study, we tested for compounds which had the potential to inhibit the Alzheimer's amyloid Aβ protein from forming fibrils over a 1 week period. Thus, compounds identified have the ability to inhibit Alzheimer's amyloid fibril formation. For these studies, 25 μM of Aβ (1–40)(Bachem Inc., Torrance, Calif., USA; Lot #WM365) was incubated in microcentrifuge tubes at 37° C. for 1 week (in triplicate), either alone, or in the presence of 1.25 mM (ie. 1:50 M ratio of Aβ:test compound)(except PTI-00700 which was isolated and used as described below) of various compounds in 150 mM Tris HCl, 10 mM NaCl, pH 7.0 (TBS). The compounds tested included PTI-07499 (mannose pentasulfate, potassium salt), PTI-20049 (methyl alpha-D-glucopyranoside 2,3,4,6-tetrasulfate, potassium salt), PTI-20814 (methyl alpha-D-mannopyranoside 2,3,4,6-tetrasulfate, potassium salt), PTI-70936 (sucrose heptasulfate, potassium salt), PTI-70946 (sucrose hexasulfate, potassium salt), PTI-70011(sucrose octasulfate, potassium salt) PTI-00800 (glucosamine, sulfate salt, from Enzymatic Therapy, Green Bay, Wis. and commercially known as "glucosamine sulfate"), PTI-00900 (glucosamine, sulfate salt, from Jarrows Formulas, Los Angeles, Calif. and commercially known as "glucosamine sulfate 500") and PTI-00700, (Glucosamine, sulfate salt, with *Uncaria tomentosa*). PTI-00700 was derived from preservative free capsules containing 400 mg blend of glucosamine (sulfate salt) and 50 mg of *Uncaria tomentosa*'s inner bark. For these studies, the powder within one capsule of PTI-00700 was extracted in 5 ml of distilled water and pelleted by gravity. The soluble fraction was then obtained and used in these studies at a final dilution of 1:227 in Tris-buffered saline (TBS)(comparable to the concentration of other compounds tested in terms of glucosamine).

To assess the effects of each compound on Aβ (1–40) fibril formation, 50 μl aliquots were taken from each tube for analysis at 1 hr, 1 day, 3 days, and 1 week. For each determination described above, following each incubation period, 50 μl of Aβ+/– test compounds were added to 1.2 ml of 100 μM Thioflavin T (Sigma Chemical Co., St. Louis, Mo.) in 50 mM $NaPO_4$ (pH 6.0). Studies indicated that increasing concentrations of Aβ gave a proportional increase in fluorescence in the presence of 100 μM Thioflavin T, ruling out the presence of any disproportionate inner filter effects in these studies. Fluorescence emission at 482 nm was measured on a Turner instrument-model 450 fluorometer at an excitation wavelength of 450 nm. For each determination, the fluorometer was calibratedby zeroing in the presence of the Thioflavin T reagent alone, and by setting the 50 ng/ml riboflavin (Sigma Chemical Co., St. Louis, Mo.) in the Thioflavin T reagent to 1800 fluorescence units. All fluorescence determinations were based on these references and any fluorescence given off by any of the compounds in the presence of the Thioflavin T reagent was always subtracted from all pertinent readings.

For all fibrillogenesis studies utilizing Thioflavin T fluorometry, as disclosed herein, comparisons of amyloid protein in the presence or absence of test compounds were based on paired Student's t tests with data shown as mean +/– standard deviation. Significance was reported at the 95% ($p<0.05$), 99% ($p<0.01$) and 99.999% ($p<0.001$) confidence levels.

As shown in FIG. 1, the effects of these various test compounds on Alzheimer's Aβ (1–40) amyloid fibril formation was evaluated over a 1-week incubation period. Freshly suspended Aβ (1–40) alone, following a 1-hour incubation at 37° C., demonstrated an initial fluorescence of 75+/–9 fluorescence units. During the 1-week incubation period, there was a gradual increase in the fluorescence of Aβ (1–40) alone, increasing 6.1-fold from 1 hour to 1 week, with a peak fluorescence of 459 +/–18 fluorescence units observed at 1 week (FIG. 1), consistent with previous studies (Castillo et al, *J. Neurochem.* 69:2452–2465, 1997). Of all the compounds tested, only glucosamine (sulfate salt) containing *Uncaria tomentosa* (ie. PTI-00700) significantly inhibited Aβ (1–40) amyloid fibril formation. Glucosamine (sulfate salt) derived from two different sources (ie. PTI-00800 and PTI-00900) which did not contain *Uncaria tomentosa* did not significantly inhibit Aβ (1–40) amyloid fibril formation (FIG. 1). This indicated that the active amyloid inhibitory agent was most likely *Uncaria tomentosa*. The significant inhibition of Aβ amyloid fibril formation by glucosamine (sulfate salt) containing *Uncaria tomentosa* (ie. PTI-00700) was detected as early as 1 hour of incubation. Significant inhibition ($p<0.001$) by glucosamine (sulfate salt) containing *Uncaria tomentosa* on Aβ amyloid fibril formation was observed at all time points including 1 hour, 1 day, 3 days and 1 week. By 1 week, glucosamine (sulfate salt) containing *Uncaria tomentosa* was effective in significantly ($p<0.001$) inhibiting amyloid fibril formation by 78%. This initial data indicated that glucosamine (sulfate salt) containing *Uncaria tomentosa* was a potent inhibitor of Alzheimer's amyloid fibril formation.

Example 2

Uncaria tomentosa is the Active Agent and a Potent Inhibitor of Alzheimer's Aβ (1–40) Amyloid Fibril Formation The next studies were designed to reproduce some of the data initially acquired and to determine if the active agent which inhibited Aβ amyloid fibril formation was in fact *Uncaria tomentosa*. In these studies, the effects of various compounds on Alzheimer's Aβ (1–40) fibrillogenesis were again assessed using Thioflavin T fluorometry. For these studies, 25 μM of Aβ (1–40)(Bachem Inc., Torrance, Calif., USA; Lot #WM365) was incubated in microcentrifuge tubes at 37° C. for 1 week (in triplicate), either alone, or in the presence of 1.25 mM (ie. 1:50 M ratio of Aβ:test compound) of various compounds (except PTI-00700, PTI-00701 and PTI-00703 which were isolated and used as described below) in 150 mM Tris HCl, 10 mM NaCl, pH 7.0 (TBS). The compounds tested included glucosamine (sulfate salt) containing *Uncaria tomentosa* (PTI-00700), glucosamine (sulfate salt) containing *Uncaria tomentosa* which was filtered through a filter containing a 30 kilodalton cutoff (PTI-00700<30 kDa), glucosamine (hydrochloride salt) containing *Uncaria tomentosa* (PTI-00701), pure glucosamine (PTI-00712; molecular weight=216; obtained from the Sigma Chemical Company, St. Louis, Mo., USA), pure galactosamine (PTI-00713; molecular weight=216; obtained from the Sigma Chemical Company, St. Louis, Mo., USA), sodium sulfate (PTI-00725; molecular weight=142; obtained from the Sigma Chemical Company, St. Louis, Mo., USA), and *Uncaria tomentosa* (PTI-00703; obtained from a commercial source). For these studies, the powder within one gelatin-coated capsule of glucosamine sulfate containing *Uncaria tomentosa* (PTI-00700) was extracted in 5 ml of distilled water and used for testing as described in Example 1. The powder within one gelatin-coated capsule of glucosamine (hydrochloride salt) containing *Uncaria tomentosa* (PTI-00701) was extracted in 5 ml of distilled water and used at a final dilution of 1:40 in TBS (which represented the total extract derived from 250 μg of *Uncaria tomentosa* per ml), whereas the powder within one gelatin-coated capsule of *Uncaria tomentosa* (PTI-00703) was extracted in 5 ml of distilled water and used at a final dilution of 1:250 in TBS (which represented the total extract derived from 350 μg of *Uncaria tomentosa* per ml).

Figure 2:
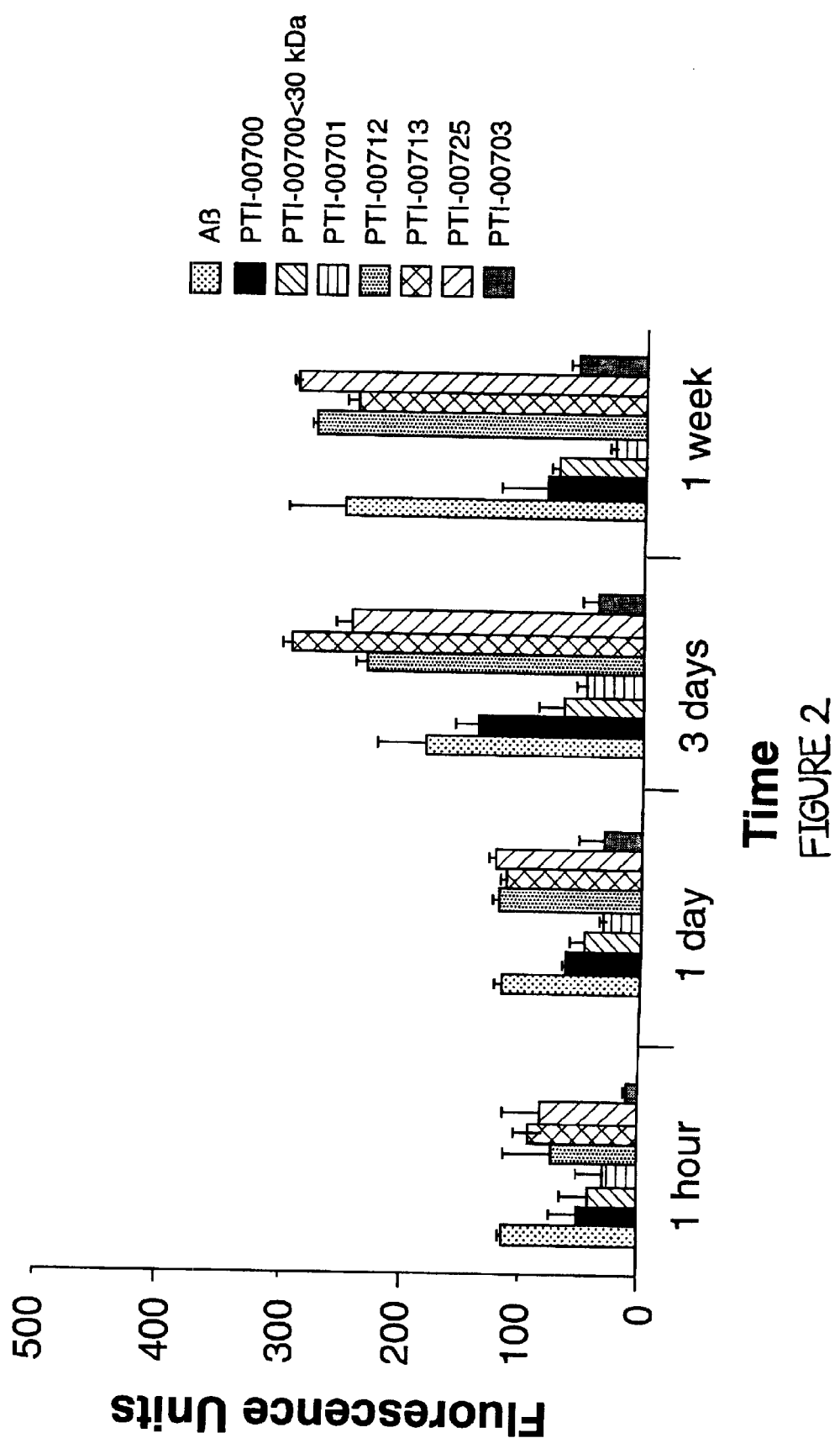
FIG. 2 is a black and white graph of a 1 week Thioflavin T fluorometry assay utilized to identify inhibitors of Alzheimer's Aβ (1–40) amyloid fibril formation. Glucosamine (sulfate salt) containing *Uncaria tomentosa* (PTI-00700), glucosamine (sulfate salt) containing *Uncaria tomentosa* (PTI-00700<30 kDa) which had gone through a filter with molecular weight cutoff of 30 kDa (PTI-00700<30 kDa), glucosamine (hydrochloride salt) containing *Uncaria tomentosa* (PTI-00701), and pure *Uncaria tomentosa* (PTI-00703) are all shown to be effective inhibitors of Alzheimer's Aβ amyloid fibril formation.

To assess the effects of each compound on Alzheimer's Aβ (1–40) fibril formation, 50 μl aliquots were taken from each tube for analysis at 1 hr, 1 day, 3 days, and 1 week using Thioflavin T fluorometry as described above. As shown in FIG. 2, the effects of these various test compounds on Aβ (1–40) amyloid fibril formation was evaluated over a 1-week incubation period. Freshly suspended Aβ (1–40) alone, following a 1-hour incubation at 37° C., demonstrated an initial fluorescence of 113+/−7 fluorescence units. During the 1-week incubation period, there was a gradual increase in the fluorescence of Aβ (1–40) alone, increasing 2.2-fold from 1 hour to 1 week, with a peak fluorescence of 250+/−50 fluorescence units observed at 1 week. Glucosamine (sulfate salt) containing *Uncaria tomentosa* (PTI-00700), and glucosamine (sulfate salt) containing *Uncaria tomentosa* which was filtered through a filter containing a 30 kilodalton cutoff (PTI-00700<30 kDa) were both potent inhibitors of Aβ amyloid fibril formation causing a 68% and 72% inhibition at 1 week, respectively (FIG. 2). An even more potent inhibition of amyloid fibril formation was observed with glucosamine (hydrochloride salt) containing *Uncaria tomentosa* (PTI-00701) causing a 90% inhibition of Aβ amyloid fibril formation by 1 week. Each of these potent compounds significantly inhibited amyloid fibril formation as early as 1 hour following incubation. The active ingredient which was deemed to cause this potent inhibitory effect on amyloid fibril formation was *Uncaria tomentosa* contained within these commercial preparations. This was due to the fact that glucosamine (PTI-00712) which did not contain *Uncaria tomentosa* had no inhibitory effect on amyloid fibril formation whatsoever. In addition, pure *Uncaria tomentosa* (PTI-00703) caused a similar inhibitory effect (73% inhibition at 1 week; and a 93% inhibition at 1 hour) on amyloid fibril formation to that observed with glucosamine (sulfate salt) containing *Uncaria tomentosa*. These data indicated that the active ingredient which was a potent inhibitor of Alzheimer's disease amyloid fibril formation was *Uncaria tomentosa*.

Example 3

Glucosamine (Sulfate Salt) Containing *Uncaria tomentosa* (PTI-00700) Inhibits Alzheimer's Amyloid Fibril Growth In Alzheimer's disease and other amyloidoses, amyloid fibril growth is believed to involve amyloid protein self-interactions (ie. Aβ—Aβ interactions). Any potential effective therapeutic agent for amyloid deposition, accumulation and/or persistence should also be capable of causing an inhibition of amyloidprotein self-interactions. This is important for preventing any new amyloid fibril formation when treating Alzheimer's disease patients at early stages of the disease. ELISA methodologies (i.e. solid phase binding assays) were therefore used to identify compounds which were capable of inhibiting Aβ—Aβ interactions (i.e. Alzheimer's amyloid fibril growth).

Aβ (1–40) was first labelled with biotin according to the following protocol. 1 mg of Aβ (1–40) (Bachem Inc., Torrance, Calif., USA; Lot #WL934) was dissolved in 200 μl of PBS (pH 8.0) and incubated for 1 week at 37° C. The fibrillar Aβ solution was then added to 0.2 mg of a biotinylation agent [(sulfosuccinimidyl-6-(biotinamido) hexanoate)](sulfo-NHS-LC-Biotin) and incubated for 45 minutes at room temperature (according to the manufacturer's protocol; Pierce). To remove excess sulfo-NHS-LC-Biotin not incorporated into Aβ, 25 μl of 3 M sodium acetate and 1 ml of ethanol were added to the solution, vortexed and then centrifuged at 14,000 ×g for 20 minutes. The supernatant was then discarded and the pellet was resuspended in 200 μl of distilled water, and reprecipitated with ethanol containing 2.5% of 3M sodium acetate. The centrifugation steps (described above) were then repeated. The pellet which contained fibrillized Aβ which was biotinylated (at the non self-interacting region of Aβ) was then resuspended in 1 ml of distilled deionized water. The amount of biotin incorporated was then determined using the HABA (2-(4'-hydroxyazo-benzene)benzoic acid) method (according to the manufacturer's protocol; Pierce).

2 μg of unlabelled Aβ in 40 μl of Tris-buffered saline containing 100 mM Tris-HCl, 50 mM NaCl, 3 mM $NaN_3$, pH 7.0 (TBS) was allowed to bind overnight at 4° C. to microtiter wells (Nunc plates, Maxisorb). The next day all of the microtiter wells were blocked for 2 hours by incubating with 300 μl of TBS with 0.05% Tween-20 (TTBS) plus 2% bovine serum albumin (BSA)(obtained from the Sigma Chemical Company, St. Louis, Mo., USA). Then, 100 μl of biotinylated Aβ1–40 in TTBS, in the presence or absence of 1.25 mM of test compounds (described below) were placed in wells (in triplicate) containing substrate bound unlabelled Aβ or blank, and allowed to bind overnight at 4° C. The next day, the wells were rinsed 3 times with TTBS, and then probed for 2 hours with 100 μl of streptavidin-peroxidase or anti-biotinperoxidase (1:500 dilution of a 2 μg/ml solution) (Sigma Chemical Co., St. Louis, Mo.) in TTBS containing 0.1% BSA. The wells were then rinsed 3 times with TTBS and 100 μl of a substrate solution (OPD-Sigma Fast from Sigma Chemical Co., St. Louis, Mo.) was added to each well and allowed to develop for 5 minutes or until a significant color change was observed. The reaction was stopped with 50 μl of 4N $H_2SO_4$ and read on a Model 450 microplate reader (Biorad, Hercules, Calif., USA) at 490 nm.

The compounds tested included sucrose octasulfate (PTI-70011), sucrose hexasulfate (potassium salt)(PTI-70946), sucrose heptasulfate (potassium salt)(PTI-70936), methyl alpha-D-mannopyranoside 2,3,4,6-tetrasulfate (potassium salt)(PTI-20814), methyl alpha-D-glucopyranoside 2,3,4,6-tetrasulfate (potassium salt)(PTI-20049), glucosamine (sulfate salt)(Enzymatic Therapy, Green Bay, Wis.)(PTI-00800), glucosamine (sulfate salt from Jarrows Formulas, Los Angeles, Calif., commercially known as "glucosamine sulfate 500") (PTI-00900), glucosamine (sulfate salt) containing Uncaria tomentosa (PTI-00700), heparin (PTI-H98546), chondroitin-4-sulfate (PTI-C45770), and dermatan sulfate (PTI-D58901). Glucosamine (sulfate salt) containing Uncaria tomentosa (PTI-00700) was isolated and used at a dilution of 1:227 in Tris-buffered saline containing 0.05% Tween-20 (TTBS), as described in Example 2.

Figure 3:
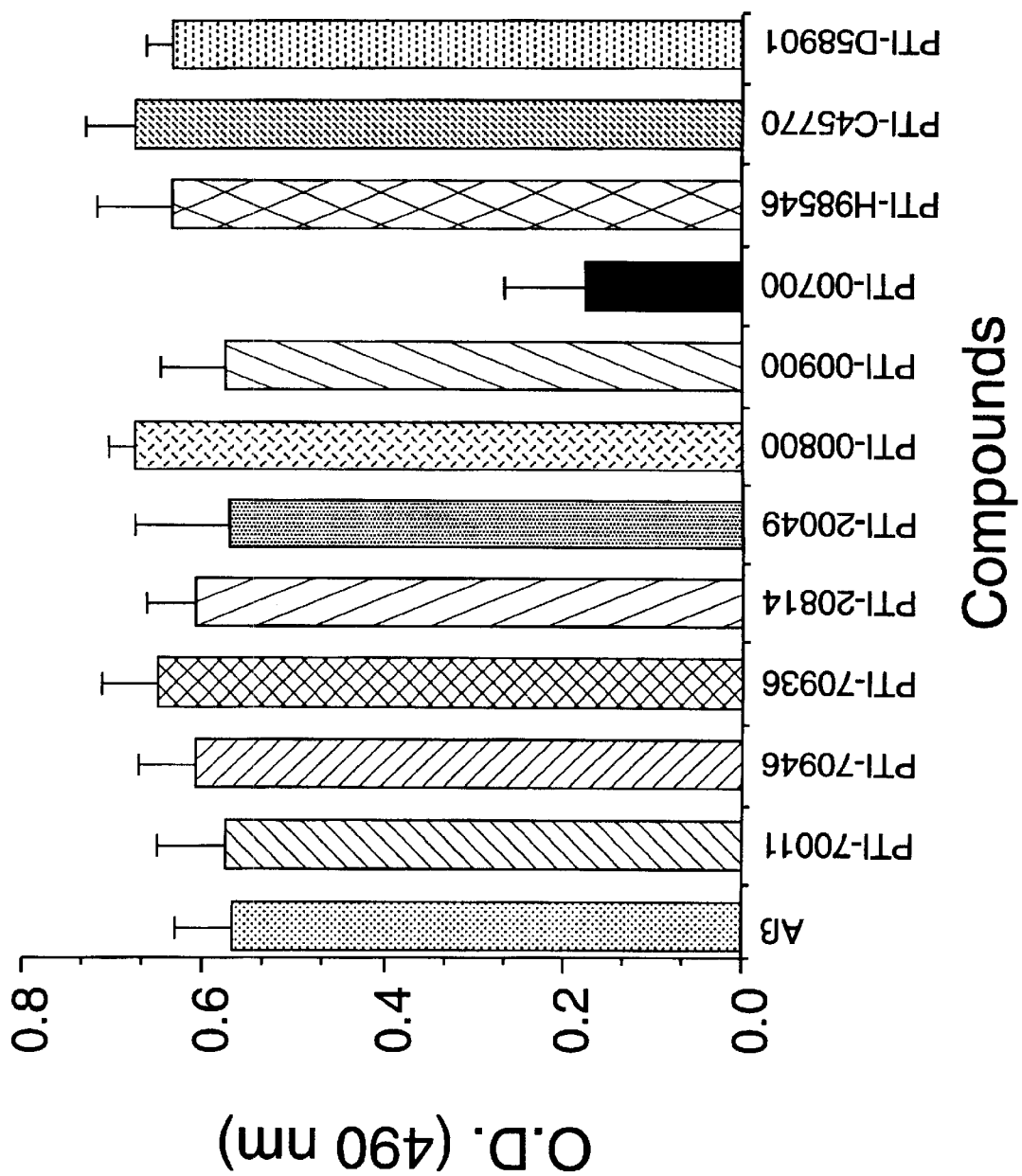
FIG. 3 is a black and white graph of a solid phase binding assay utilized to identify lead compounds which inhibit Alzheimer's Aβ—Aβ interactions (i.e. Alzheimer's amyloid fibril growth). Glucosamine (sulfate salt) containing *Uncaria tomentosa* (PTI-00700) is identified as a potent inhibitor of Alzheimer's amyloid fibril growth.

As shown in FIG. 3, only glucosamine (sulfate salt) containing Uncaria tomentosa (PTI-00700) was effective in causing a significant ($p<0.001$) 70% reduction in $A\beta$—$A\beta$ interactions. The active ingredient which caused this inhibition was Uncaria tomentosa, since pure glucosamine (sulfate salt) obtained from two different sources (ie. PTI-00800 and PTI-00900) had no inhibitory effects on amyloid fibril growth whatsoever (FIG. 3). These data demonstrated that glucosamine (sulfate salt) containing Uncaria tomentosa was an effective inhibitor of $A\beta$—$A\beta$ interactions, and that the active ingredient which was a potent inhibitor of Alzheimer's disease amyloid fibril growth was Uncaria tomentosa.

Example 4

Glucosamine (Sulfate Salt) Containing Uncaria tomentosa Inhibit Aβ-Proteoglycan/Glycosaminoglycan Interactions in a Dose-Dependent Manner One study was implemented to determine whether glucosamine (sulfate salt) containing Uncaria tomentosa was an effective inhibitor of Aβ-proteoglycan/glycosaminoglycan (PG/GAG) interactions. Since PGs/GAGs have been found to accumulate in amyloid deposits and are believed to prevent the body's natural ability to remove unwanted "amyloid" (reviewed in Snow and Wight, Neurobiology Aging 10:481–497, 1989), an inhibitor of Aβ-PG/GAG interactions is a desirable additional target for an amyloid therapeutic. In this study a solid phase binding immunoassay was utilized to determine whether glucosamine (sulfate salt) containing Uncaria tomentosa (PTI-00700) was an effective inhibitor of Aβ-PG/GAG interactions and whether this inhibition occurred in a dose-dependent manner.

12 μg of perlecan (isolated from the Engelbreth-Holm-Swarm sarcoma)(Castillo et al, J. Biochemistry 120:433–444, 1996), heparin (molecular weight=5 kDa; obtained from the Sigma Chemical Company, St. Louis, Mo., USA) or heparan sulfate (molecular weight =~70 kDa; obtained from Seikagaku America, Rockville, Md.) in 80 μl of Tris-buffered saline containing 100 mM Tris-HCl, 50 mM NaCl, 3 mM $NaN_3$, pH 9.0 (TBS) was allowed to bind overnight at 4° C. to microtiter wells (Nunc plates, Maxisorb). The next day all of the microtiter wells were blocked for 2 hours by incubating with 300 μl of TBS with 0.05% Tween-20 TTBS) plus 1% bovine serum albumin (BSA)(obtained from the Sigma Chemical Company, St. Louis, Mo., USA). Then, 100 μl of Aβ1–40 (5 μM) (Bachem Inc., Torrance, Calif., USA; Lot #WM365) in TTBS containing 0.05% albumin in the presence or absence of 5 μl of glucosamine (sulfate salt) containing Uncaria tomentosa (PTI -00700) were placed in wells (in triplicate) containing substrate bound PG/GAG or blank, and allowed to bind overnight at 4° C. For the study, a water extract of glucosamine (sulfate salt) containing Uncaria tomentosa (i.e. PTI-00700) was derived by taking the powder from 1 gelatin-coated capsule/pill (which contains 50 mg of Uncaria tomentosa) and extracting two times with 2.5 ml of double distilled water and then pooling the two water extracts together (referred to as the "PTI-00700 solution"). The PTI-00700 solution was then used undiluted (which represented 1/1,000th of a single pill), or diluted at ratios of 1:3 (i.e. 1/3,000th of a single pill), 1:9 (i.e. 1/9,000th of a single pill) or 1:27 (1/27,000th of a single pill), with distilled water. The next day, the wells were rinsed once with TTBS, and then probed for 45 minutes with 100 μl of anti-6E10 (Senetek, Maryland Heights, Mo.)(which recognizes Aβ 1–17) diluted 1:1000 with TTBS. This was followed by rinsing once with TTBS and probed for 45 minutes with biotinylated goat-anti mouse (diluted 1:1000) containing streptavidin-peroxidase or anti-biotinperoxidase (1:500 dilution of a 2 μg/ml solution)(Sigma Chemical Co., St. Louis, Mo.) in TTBS containing 0.1% BSA. The wells were then rinsed 3 times with TTBS and 100 μl of a substrate solution (OPD-Sigma Fast from Sigma Chemical Co., St. Louis, Mo.) was added to each well and allowed to develop for 5 minutes or until a significant color change was observed. The reaction was stopped with 50 μl of 4N $H_2SO_4$ and read on a Model 450 microplate reader (Biorad, Hercules, Calif., USA) at 490 nm.

Figure 4:
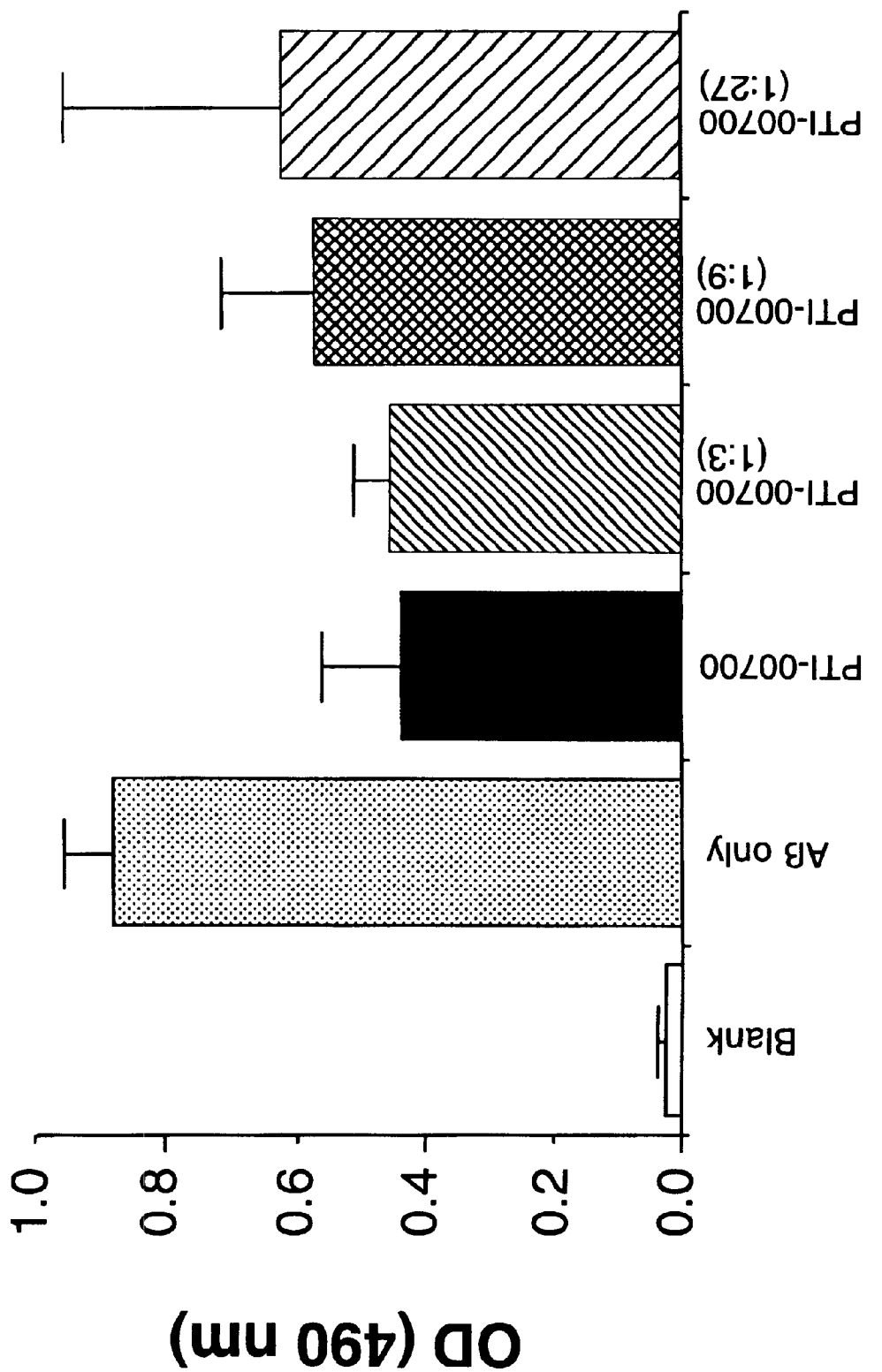
FIG. 4 is a black and white graph of a solid phase binding immunoassay utilized to determine the potential dose-dependent effects of glucosamine (sulfate salt) containing *Uncaria tomentosa* (PTI-00700) on inhibition of Aβ-proteoglycan/glycosaminoglycan (PG/GAG) interactions. Significant dose-dependent inhibition of Aβ-PG/GAG interactions is observed with treatment of glucosamine (sulfate salt) containing *Uncaria tomentosa*.
Figure 5:
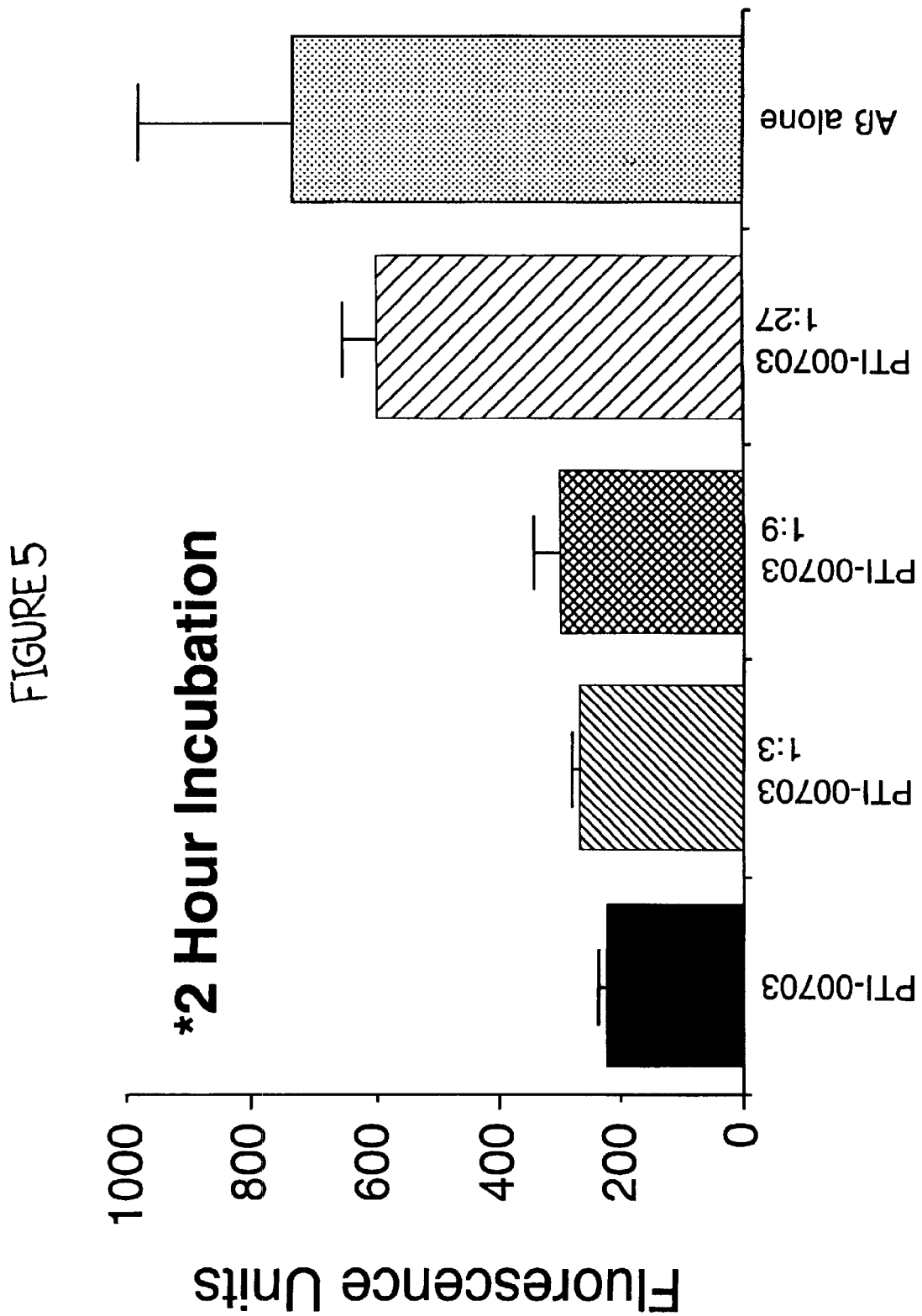
FIG. 5 is a black and white graph of a Thioflavin T fluorometry assay utilized to determine the potential dose-dependent effects of *Uncaria tomentosa* extract (PTI-00703) on dissolution/disruption of pre-formed Alzheimer's Aβ (1–40) amyloid fibrils within a 2 hour incubation period. *Uncaria tomentosa* extract causes dissolution of pre-formed Alzheimer's Aβ amyloid fibrils in a dose-dependent manner.

As shown in FIG. 4, undiluted glucosamine (sulfate salt) containing Uncaria tomentosa (PTI-00700)(which represented 1/1,000th of a single pill) was very effective (by 64%) in inhibition of Aβ-heparin/heparan sulfate interactions. A significant ($p<0.001$)49% inhibition was also observed with a 1:3 dilution (i.e. 1/3,000th of a single pill) of PTI-00700, whereas a 1:9 dilution (1/19,000th of a single pill) of PTI-00700 still caused a significant ($p<0.01$) 35% inhibition. A 1:27 dilution (i.e. 1/27,000th of a single pill) of PTI-00700 was found not to cause a significant inhibition of Aβ-heparin/heparan sulfate binding. These data demonstrated that glucosamine (sulfate salt) containing Uncaria tomentosa was also capable of inhibiting Aβ-PG/GAG interactions in a dose-dependent manner.

Example 5

Uncaria tomentosa Causes a Dissolution of Pre-Formed Alzheimer's Disease Amyloid Fibrils in a Dose-Dependent Manner and Within a 2-Hour Period One study was implemented to determine whether a relatively pure Uncaria tomentosa extract was capable of causing a "dissolution" or "disruption" of pre-formed Alzheimer's disease amyloid fibrils. This type of activity would be important for any potential anti-amyloid drug which can be used in patients who already have substantial amyloid deposition in organs and/or tissues. For example, Alzheimer's disease patients in mid-to late stage disease have abundant amyloid deposits in their brains as part of both neuritic plaques and cerebrovascular amyloid deposits. A natural therapeutic agent capable of causing dissolution of pre-existing amyloid would be advantageous for use in these patients who are at latter stages of the disease process.

For this study, 1 mg of Aβ (1–40)(Bachem Inc., Torrance, Calif., USA; Lot #WM365) was dissolved in 1.0 ml of double distilled water (1 mg/ml solution) and then incubated at 37° C. for 1 week to cause abundant Alzheimer's amyloid fibril formation. 6 μl (25 μM) of fibrillized Aβ was then incubated for 2 hours at 37° C., in the presence or absence of 1.5 μl of *Uncaria tomentosa* (PTI-00703)(described below) dissolved in 37.5 μl of double distilled water, and 15 μl containing 150 mM Tris HCl, 10 mM NaCl, pH 7.0. Following a 2 hour incubation, 50 μl aliquots were added to 1.2 ml of 100 μM Thioflavin T (Sigma Chemical Co., St. Louis, Mo.) in 50 mM $NaPO_4$ (pH 6.0) for fluorometry readings as described in Example 1 above.

For this study, the compounds tested included a water extract of *Uncaria tomentosa* which was derived by taking the powder from 10 gelatin-coated capsules of *Uncaria tomentosa* (which contain ~350 mg of *Uncaria tomentosa* per capsule) and extracting two times with 25 ml of double distilled water, and then pooling the two water extracts together (referred to as "*Uncaria tomentosa* solution"). The *Uncaria tomentosa* solution was then used either undiluted (which represents 1/3,333th of a single pill), or further diluted in distilled water at ratios of 1:3 (i.e. 1/10,000th of a single pill), 1:9 (i.e. 1/30,000th of a single pill) or 1:27 (1/90,000th of a single pill).

As shown in FIG. 4, undiluted (i.e. 1/3,333th of a single pill) *Uncaria tomentosa* (PTI-00703) was extremely effective, and caused a 70% dissolution of pre-formed Alzheimer's Aβ amyloid fibrils within the 2-hour incubation period. A significant ($p<0.001$) 63% dissolution of pre-formed Alzheimer's Aβ amyloid fibrils was also observed with a 1:3 dilution (i.e. 1/10,000th of a single pill) of an *Uncaria tomentosa* solution, whereas a 1:9 dilution (i.e. 1/30,000th of a single pill) of an *Uncaria tomentosa* solution still caused a significant ($p<0.01$) 60% dissolution. On the other hand, a 1:27 dilution (i.e. 1/90,000th of a single pill) of an *Uncaria tomentosa* solution did not cause a significant dissolution of pre-formed Aβ amyloid fibrils. These data demonstrated that *Uncaria tomentosa* causes dissolution of pre-formed Alzheimer's disease amyloid fibrils in a dose-dependent manner. Confirmation of the "dissolution effect" of *Uncaria tomentosa* on Alzheimer's disease amyloid fibrils was demonstrated by Congo red staining assays, whereby a marked reduction of congophilia (i.e. red/green birefringence when viewed under polarized light, and which represents a dissolution/disruption of the amyloid fibrillar structure) was observed when Aβ amyloid fibrils were treated with *Uncaria tomentosa* for 2 hours (not shown).

Example 6

*Uncaria tomentosa* in Liquid Form and from Another Commercial Source also Causes Dissolution of Pre-Formed Alzheimer's Disease Amyloid Fibrils The next study determined whether *Uncaria tomentosa* derived from another commercial source (referred to as PTI-00703-2) was also effective in causing dissolution/disruption of pre-formed Alzheimer's disease Aβ (1–40) amyloid fibrils. This study also addressed whether an extract derived from *Uncaria tomentosa* in liquid form (commercially available for oral consumption by humans) caused a similar dissolution of pre-formed Aβ amyloid fibrils as observed using *Uncaria tomentosa* derived from gelatin-coated capsule form. For this study, the protocol described in example 5 as described above was used. Briefly, 1 mg of Aβ (1–40)(Bachem Inc., Torrance, Calif., USA; Lot #WM365) was dissolved in 1.0 ml of double distilled water (1 mg/ml solution) and then incubated at 37° C. for 1 week. 6 μg (25 μM) of fibrillized Aβ was then incubated for 2 hours at 37° C., in the presence or absence of 1.5 μl of liquid-derived *Uncaria tomentosa* (PTI-00703-2) dissolved in 37.5 μl of double distilled water, and 15 μl containing 150 mM Tris HCl, 10 mM NaCl, pH 7.0. Following a 2 hour incubation, 50 μl aliquots were added to 12 ml of 100 μM Thioflavin T (Sigma Chemical Co., St. Louis, Mo.) in 50 mM $NaPO_4$ (pH 6.0) for fluorometry readings as described in example 1.

Figure 6:
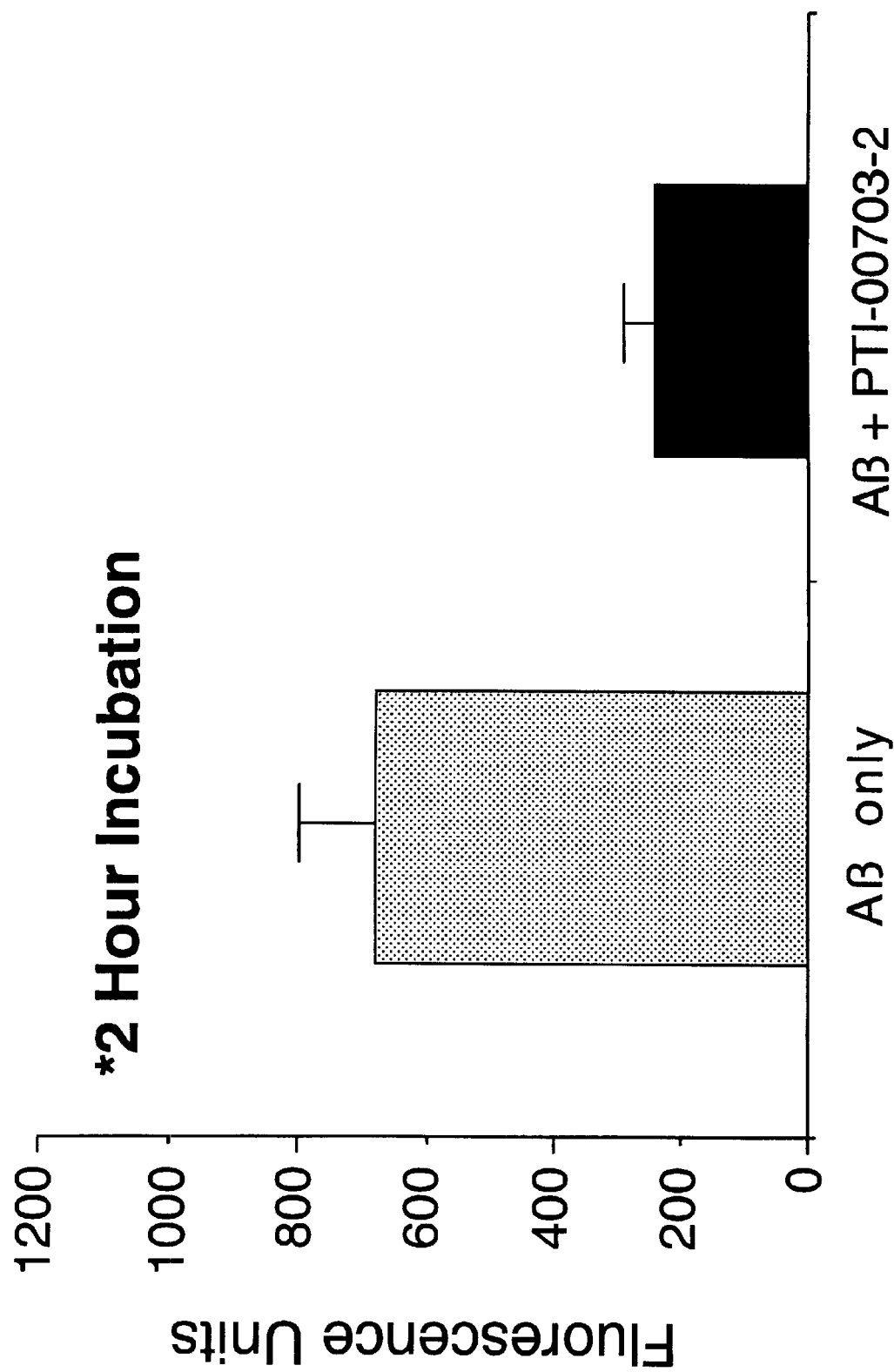
FIG. 6 is a black and white graph of a Thioflavin T fluorometry assay utilized to show that *Uncaria tomentosa* extract obtained from another commercial source (referred to as PTI-00703-02), and from *Uncaria tomentosa* in liquid form, is also able to cause significant dissolution/disruption of pre-formed Alzheimer's Aβ (1–40) amyloid fibrils within a 2 hour incubation period.

As shown in FIG. 6, liquid-derived *Uncaria tomentosa* was extremely effective in causing a dissolution/disruption of pre-formed Aβ amyloid fibrils. A significant ($p<0.001$) 70% dissolution of pre-formed Aβ amyloid fibrils was observed using liquid-derived *Uncaria tomentosa* within a 2-hour incubation period. This study demonstrated that *Uncaria tomentosa* was an effective dissolver of pre-formed Alzheimer's disease amyloid fibrils regardless of the source of *Uncaria tomentosa*, and regardless of whether the *Uncaria tomentosa* used was in solid (ie. capsule) or liquid form.

Example 7

Dose-Dependent Dissolution of Pre-Formed Alzheimer's Disease Amyloid Fibrils by *Uncaria tomentosa* Extract Obtained from a Third Commercial Source The next study determined whether *Uncaria tomentosa* obtained from yet another commercial source was also effective in causing dissolution/disruption of pre-formed Alzheimer's disease amyloid fibrils. For this study, *Uncaria tomentosa* was obtained from the powder within gelatin-coated capsules from a third commercial source (referred to as PTI-00703-R) and used as described below. For this study, a single gelatin-coated capsule containing pure *Uncaria tomentosa* was opened and the brown powder content was extracted with 1 ml of propanol followed by centrifugation (14,000×g for 15 minutes). 0.1 μl of the propanol extract was measured at 490 nm and found to demonstrate 0.0004 OD units. The fibril dissolution assay was used as described in example 5 using 0.1 μl (i.e. 1 μl was diluted with double distilled water at a 1:10 dilution and 1 μl was used), 1 μl, 2 μl and 4 μl of the PTI-00703-R extract. These amounts represented 1/10,000th, 1/1000th, 1/500th, and 1/250th of the total extract from a single pill, respectively.

Figure 7:
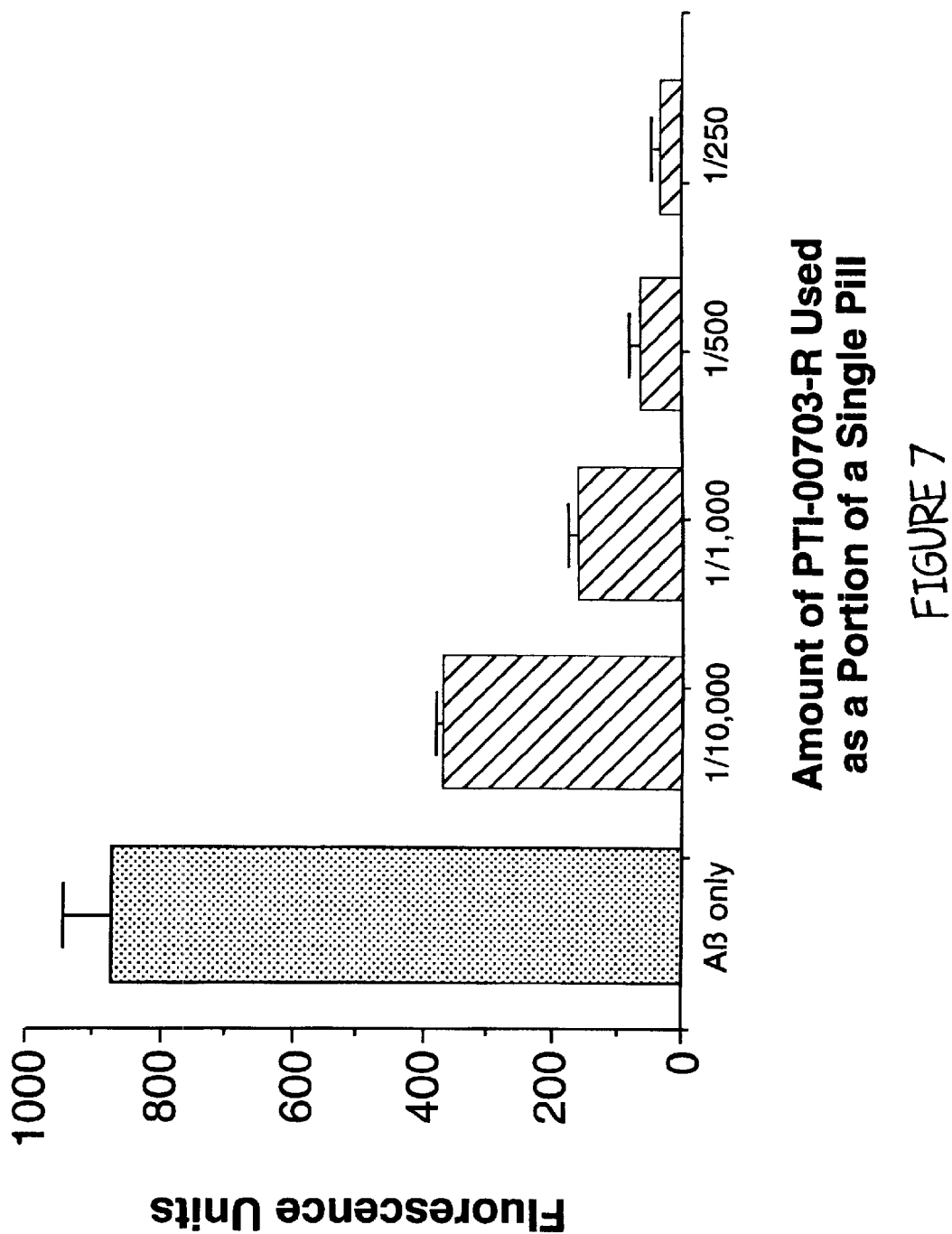
FIG. 7 is a black and white graph of a Thioflavin T fluorometry assay utilized to show that *Uncaria tomentosa* extract obtained from yet another commercial source (referred to as PTI-00703-R) is able to cause significant dose-dependent dissolution/disruption of pre-formed Alzheimer's Aβ (1–40) amyloid fibrils within a 2-hour incubation period. 1/10,000th of the extract from *Uncaria tomentosa* contained within a single gelatin-coated pill caused a significant (p<0.001) 58% dissolution, whereas 1/1,000th of a single pill *Uncaria tomentosa* extract caused a significant (p<0.001) 81% dissolution, 1/500th of a single pill *Uncaria tomentosa* extract caused a significant (p<0.001) 93% dissolution, and 1/250th of a single pill *Uncaria tomentosa* extract caused a significant (p<0.001) 97% dissolution.

As shown in FIG. 7, *Uncaria tomentosa* obtained from a single gelatin-coated capsule or pill caused a dose-dependent dissolution/disruption of Alzheimer's Aβ amyloid fibrils and within a 2-hour incubation period. A 1/10,000th portion obtained from a single capsule caused a significant ($p<0.001$) 58% dissolution, whereas a 1/1,000 portion obtained from a single capsule caused a significant ($p<0.001$) 81% dissolution. A 1/500 portion from a single capsule caused a significant ($p<0.001$) 93% dissolution, whereas a 1/250th portion from a single pill caused a significant ($p<0.001$) 97% dissolution. This study demonstrated that *Uncaria tomentosa* obtained from yet another source was a potent agent causing dose-dependent dissolution of pre-formed Alzheimer's disease amyloid fibrils. In addition, the diluted contents from a single gelatin-coated capsule/pill of *Uncaria tomentosa* (which is currently orally consumed by humans) was still extremely effective in causing a dissolution/disruption of Alzheimer's disease pre-formed amyloid fibrils.

Example 8

*Uncaria tomentosa* Extract Causes a Dissolution of Aβ (1–42) Alzheimer's Amyloid Fibrils The amyloid fibrils of Alzheimer's disease primarily consist of Aβ in a form containing residues 1–40 or 1–42.

The longer variant of Aβ contains two hydrophobic residues which cause substantial fibril formation almost immediately (Castillo et al, *J. Neurochem.* 69:2452–2465, 1997). Aβ 1–42 is also believed to be the predominant form of Aβ existing in Alzheimer's amyloid plaques, whereas Aβ 1–40 is believed to be the predominant form of Aβ existing in Alzheimer's cerebrovascular amyloid deposits (Tamaoka et al, *Br. Res.* 679:151–156, 1995; *Biochem. Biophys. Res. Comm.* 205:834–842, 1994). The next study was therefore implemented to determine whether *Uncaria tomentosa* also causes dissolution/disruption of pre-formed Aβ (1–42) amyloid fibrils and whether this effect was long-lasting.

For this study, the method of Thioflavin T fluorometry as described in example 5 was used. Briefly, 30 μl of 250 μM of Aβ (1–42)(Bachem Biosciences, King of Prussia, Pa., USA; Lot #508780) was mixed with 7.5 μl of a *Uncaria tomentosa* stock solution (as described below), 75 μl of 4×TBS and 187.5 μl of double distilled water (pH 7.0), and incubated in microcentrifuge tubes at 37° C. for 4 days (in triplicate), either alone, or in the presence of *Uncaria tomentosa*. The water extract of *Uncaria tomentosa* (PTI-00703) was derived by taking the powder contents from 10 gelatin-coated capsules of *Uncaria tomentosa* and extracting two times with 25 ml of double distilled water. The extract was then diluted 1:250 in double distilled water (1 ml of stock solution represented the total extract derived from 350 μg of *Uncaria tomentosa*) to generate an *Uncaria tomentosa* stock solution.

Figure 8:
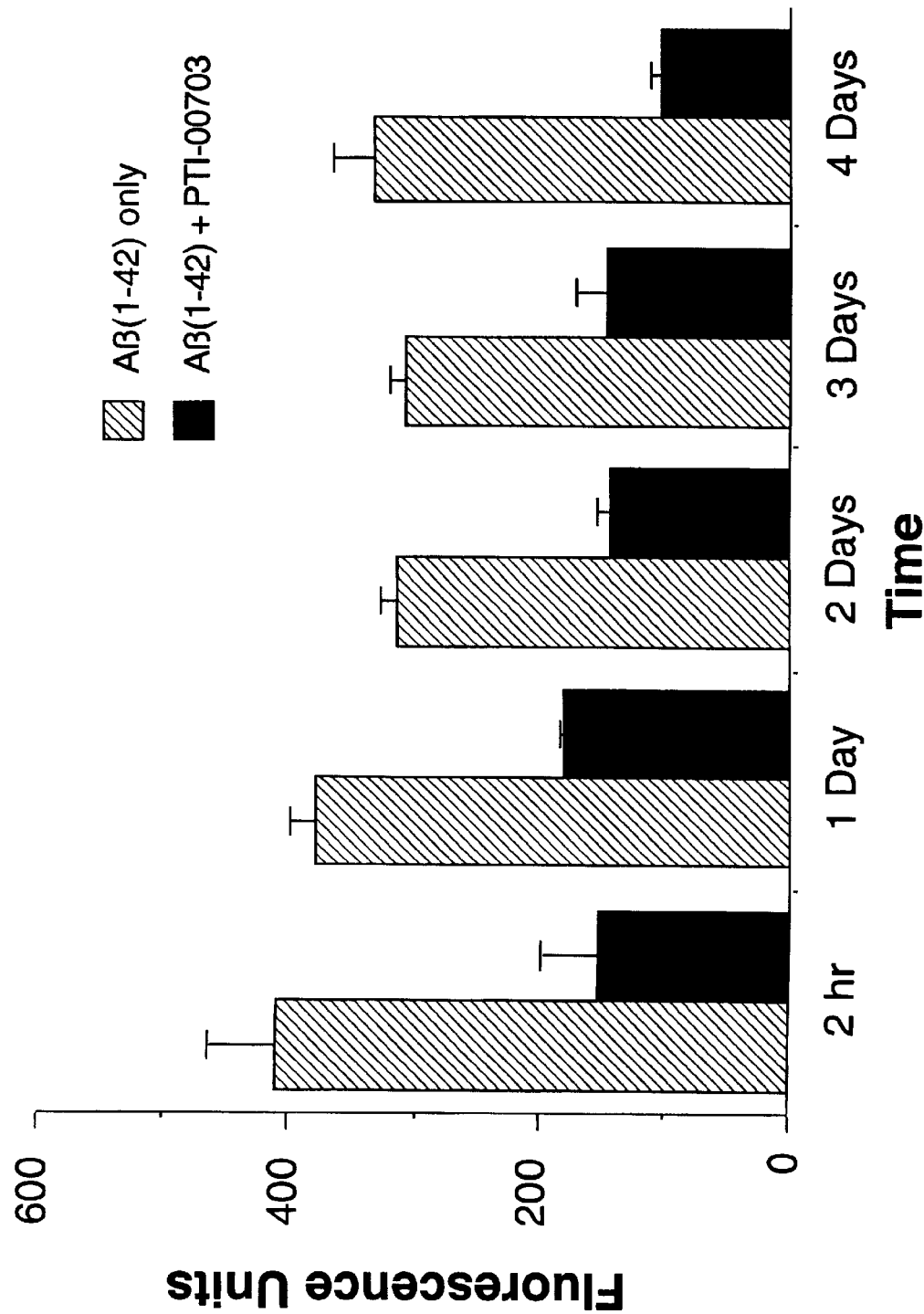
FIG. 8 is a black and white graph of a Thioflavin T fluorometry assay utilized to show that an *Uncaria tomentosa* extract (PTI-00703) is also able to cause a significant (p<0.001) dissolution of pre-formed Alzheimer's Aβ (1–42) amyloid fibrils (i.e. the longer and more fibrillogenic form of Alzheimer's amyloid) at all time points, with a 63% dissolution/inhibition observed as early as 2 hours of incubation.

As shown in FIG. 8, freshly suspended Alzheimer's Aβ (1–42) alone, following a 2-hour incubation at 37° C., demonstrated an initial fluorescence of 409+/–46 fluorescence units. During the 4 day incubation period, the levels of Aβ (1–42) amyloid fibrils as determined by Thioflavin T fluorescence remained about the same (FIG. 10). *Uncaria tomentosa* caused a significant dissolution/disruption of Aβ (1–42) amyloid fibril formation at all time points during the 4 day experiment. Since Aβ (1–42) is able to spontaneously form abundant amyloid fibrils in solution, the initial inhibition by *Uncaria tomentosa* on Aβ (1–42) fibrils at 2 hours, actually reflected *Uncaria tomentosa*'s ability to dissolve pre-formed amyloid fibrils. At 2 hours of incubation, *Uncaria tomentosa* caused a significant (p<0.001) 63% dissolution of Aβ (1–42) amyloid fibrils. A similar inhibition was observed at all time points (FIG. 8). By 4 days, a significant (p<0.001) 69% dissolution of Aβ (1–42) amyloid fibrils was still observed, indicating that the dissolving ability of *Uncaria tomentosa* on Aβ (1–42) amyloid fibrils was long-lasting.

Confirmation of the inhibitory effect of *Uncaria tomentosa* extract on Aβ (1–42) amyloid fibrils was determined by Congo red staining of aliquots taken from the above assay solutions. A marked reduction of congophilia (i.e. red/green birefringence when viewed under polarized light) was observed when Aβ amyloid fibrils were treated with *Uncaria tomentosa* for 2 hours (not shown).

Example 9

*Uncaria tomentosa* Causes Dissolution of Islet Amyloid Fibrils (Amylin)

90% of patients with type II diabetes demonstrate the deposition and accumulation of amyloid fibrils in the islets of Langerhans in the pancreas (Cooper et al, *Proc. Natl. Acad. Sci. USA* 84:8628–8632, 1987). This amyloid protein involved consists of a 37 amino acid protein known as islet amyloid polypeptide or amylin. Islet amyloid is believed to contribute to the destruction of the beta-cells of the pancreas, thus eventually leading many patients to become insulin-dependent (ie. type I diabetes). Amylin has the ability to also form substantial amyloid fibrils immediately when placed in solution. The next study was therefore implemented to determine whether *Uncaria tomentosa* also causes dissolution/disruption of another type of amyloidosis, and whether this effect was also long-lasting.

For this study, the method of Thioflavin T fluorometry as described in Example 5 was used. Briefly, 30 μl of 250 μM of human amylin (Bachem Inc, Torrance, Calif., USA; Lot #WL934) was incubated in microcentrifuge tubes at 37° C. for 4 days (in triplicate), either alone, or in the presence of 1.5 μl of *Uncaria tomentosa* (PTI-00703)(as described in Example 8).

Figure 9:
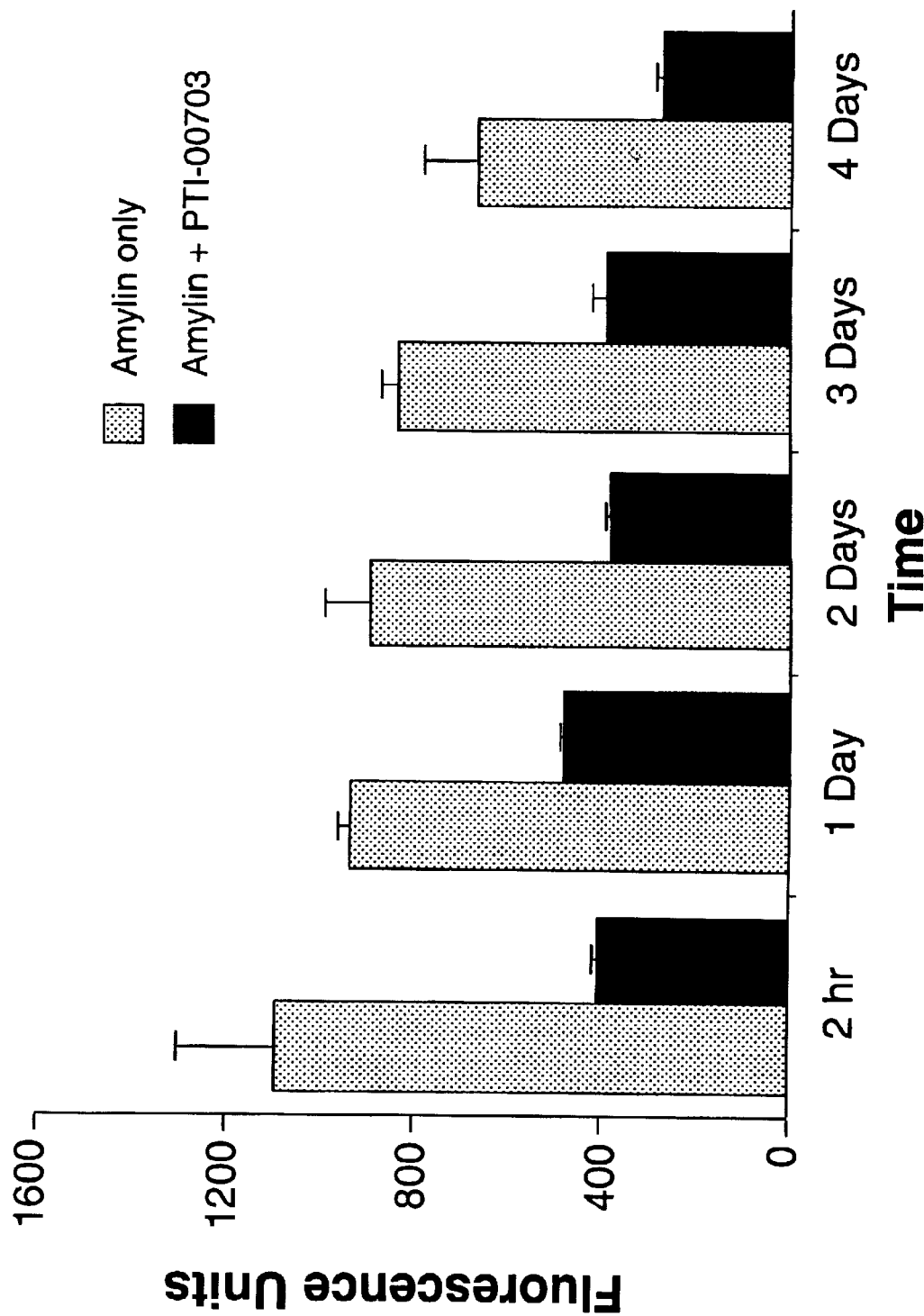
FIG. 9 is a black and white graph of a Thioflavin T fluorometry assay utilized to show that an *Uncaria tomentosa* extract (PTI-00703) is also able to cause a significant (p<0.001) dissolution of pre-formed islet amyloid fibrils (ie. amylin) at all time points, with a 72% dissolution/inhibition observed as early as 2 hours of incubation.

As shown in FIG. 9, freshly suspended amylin alone, following a 2-hour incubation at 37° C., demonstrated an initial fluorescence of 1115+/–171 fluorescence units. During the 4 day incubation period, the levels of islet amyloid fibrils as determined by Thioflavin T fluorescence were found to decrease reaching levels of 660+/–123 fluorescent units by 4 days (FIG. 9), consistent with previous studies (Castillo et al, *Diabetes* 47:612–620, 1998). *Uncaria tomentosa* (PTI-00703) was found to cause an inhibition of amylin fibril formation at all time points during the 4 day experiment. Since amylin is able to spontaneously form abundant amyloid fibrils in solution, the initial inhibition by *Uncaria tomentosa* on amylin fibrils at 2 hours, again reflected *Uncaria tomentosa*'s ability to dissolve/disrupt pre-formed amyloid fibrils. At 2 hours of incubation, *Uncaria tomentosa* (PTI-00703) caused a significant (p<0.001) 72% dissolution of amylin fibrils, whereas by 4 days, a significant (p<0.001) 80% dissolution of amylin fibrils was still observed (FIG. 9). This study demonstrated that *Uncaria tomentosa* is capable of causing significant dissolution of other forms of amyloid (such as islet amyloidosis) and that this effect was again long-lasting.

Example 10

Methods of Isolation of the Amyloid Inhibitory Ingredients within *Uncaria tomentosa*

Also disclosed are methods for isolation and identification of the active amyloid inhibitory ingredients within *Uncaria tomentosa* obtained from several different commercial sources. For isolation of the active amyloid inhibitory ingredients from gelatin-coated capsules of *Uncaria tomentosa*, 400 capsules (per run) containing dried plant materials are collected into a 1 liter polypropylene container, to which 800 ml of propanol (Fisher, Fair Lawn, N.J., USA) is added and stirred overnight at 4° C. using a magnetic stirrer. For isolation of the active amyloid inhibitory ingredients of *Uncaria tomentosa* from solid tablets, the material in 400 tablets (per run) is ground up using a mortar and pestle, and extracted with propanol as described above. The extract is then centrifuged at 17,000 ×g (Sorvall) for 20 minutes and the supernatant is collected. The extraction and centrifugation procedure is repeated 5 more times and the supernatants are collected, and then concentrated using a rotary evaporator (Rotavapor-R, Brinkman, Westbury, N.J., USA) at 60° C. When the volume is small enough (i.e. 500 mls), the extract is recentrifuged at 17,000 ×g to remove any insoluble materials. The supernatant obtained is then precipitated with 4 volumes of petroleum ether (Fisher) and the precipitate is collected following centrifugation at 3,000 ×g for 20 minutes using a Benchtop centrifuge. The pellet obtained is then washed twice by resuspension in 100 ml of distilled water, and then centrifuged again at 3,000 ×g for 20 minutes. The resulting pellet is then dissolved in 50–100 ml (depending on the size of the pellet) of propanol and applied to a 300-ml silica column equilibrated with propanol containing 0.5% (v/v) acetic acid. The same solvent is then used to elute, and the fastest-moving yellowish-brown and/or orange colored fractions are collected with fraction collector, and precipitated with 4 volumes of petroleum ether as described above. The pellet is then dissolved in acetonitrile/acetic acid/water (50:0.5:49.5; v/v/v) or HPLC injection.

The dissolved pellet is then divided into approximately 30 equal portions for injection into a HPLC (Hewlett-Packard 1050 series with multiwavelength detector and HP 3396 series integrator, Hewlett-Packard, Wilmington, Del.) with a 1×25 cm $C_{18}$ column (218 TP1010, Vydac, Hesperia, Calif.), maintained at 30° C. with a flow rate of 2 ml/min. Other columns may also be used for HPLC application, and the flow rates and eluates used to elute and purify the injected materials can be adjusted accordingly. Using the column and flow rates as described above, after injection, the sample is eluted with gradients of A and B, such that 0% B for 5 min, 0–15% B from 5–10 min., 15–45% B from 10–70 min., and 45–100% B from 70–85 min; where B=95% acetonitrile with 0.5% acetic acid in distilled water and A=5% acetonitrile with 0.5% acetic acid in distilled water. The effluents are monitored at 490 nm and 4 ml fractions are collected in a fraction collector and pooled peaks are obtained at various retention times, from 0 to 85 minutes. The fractions are then concentrated by lyophilization after most of the acetonitrile is removed by rotary evaporation. 20–30 injections is required to obtain sufficient material (50–100 mg from 4 bottles of pills) for testing in relevant assays, or for sample identification.

Another mode of isolation of the amyloid inhibitory active ingredients within *Uncaria tomentosa* obtained from different commercial sources, is similar to that described above, except the use of the silica column step is omitted. This is a quicker method which also allows for much greater yield (i.e. 300–400 mg per preparation, instead of 50–100 mg per preparation). For this method, following the extraction with propanol, precipitation and washing as described above, the washed pellets are then dissolved in acetonitrile/acetic acid/water (50:0.5:49.5; v/v/v) for HPLC injection.

The dissolved pellet is then divided into approximately 40 equal portions for injection into a HPLC (Hewlett-Packard 1050 series with multiwavelength detector and HP 3396 series integrator, Hewlett-Packard, Wilmington, Del.) with a 1×25 cm $C_{18}$ column (218TP1010, Vydac, Hesperia, Calif.), maintained at 30° C. with a flow rate of 2 ml/min. After injection, the sample is eluted with gradients of A and B, such that 0% B for 5 min, 0–15% B from 5–10 min., 15–45% B from 10–70 min., and 45–100% B 70–85 min; where B=95% acetonitrile with 0.5% acetic acid in distilled water and A=5% acetonitrile with 0.5% acetic acid in distilled water. The effluents are monitored at 490 nm and 4 ml fractions are collected in a fraction collector and pooled peaks are obtained at various retention times, from 0 to 85 minutes. The fractions are then concentrated by lyophilization after most of the acetonitrile is removed by rotary evaporation. 40–50 injections is required to obtain sufficient material (300–400 mg from 4 bottles of pills) for testing in relevant assays, or for sample identification.

FIG. 10 demonstrates that this method is effective for separation, purification and identification of the active amyloid inhibitory ingredients within *Uncaria tomentosa*. As shown in FIG. 10 A, reverse phase HPLC monitored at 490 nm (due to activity correlating with yellowish-brown and/or orange color) and eluted with a gradient as described above demonstrated that the *Uncaria tomentosa* extract contained multiple ingredients that eluted off the column with a broad peak observed at 13–45 minutes, and a peak observed at 80 minutes. Fraction 26, as an example, was re-injected onto HPLC and a symmetrical peak was obtained (FIG. 10B) indicating the polydispersity of the broad peak observed in FIG. 10A is not due to column artifact, but is due to the presence of individual components within the *Uncaria tomentosa* extract. Peaks at 26 minutes and 80 minutes were then tested for potential dissolution/disruption of pre-formed Alzheimer's Aβ amyloid fibrils (as described in Example 5) to determine if these peaks contained active amyloid inhibitory ingredients (FIG. 10C). Fraction at 26 minutes (but not at 80 minutes) exhibited potent amyloid inhibitory activity causing an 85% dissolution/disruption of pre-formed Alzheimer's disease amyloid fibrils within a 2-hour period. Other peaks (from 13 to 45 minutes retention time) were also obtained and tested as described above, and also found to contain amyloid inhibitory ingredients (not shown), suggesting that amyloid inhibitory ingredients were present within the broad peak from 13 to 45 minutes retention time. This study indicates that our method of isolation and testing can be used to purify and isolate the active amyloid inhibitory ingredients within *Uncaria tomentosa* extracts.

To identify the chemical structures and elemental composition of the active amyloid inhibitory ingredients within *Uncaria tomentosa* various analyses can be implemented, known to those skilled in the art. These include, but are not limited to: a) use of a scanning electron microscope equipped with energy dispersive x-ray analyzer to detect and spatially map some elements present in each sample, b) high resolution mass spectroscopy to determine molecular weight and elemental composition, 3) differential scanning calorimetry to determine melting point, 4) FTIR spectroscopy to determine functional groups and comparisons are made to spectral libraries, 5) proton and $C^{13}$ NMR spectroscopy for further material characterization by providing information regarding the position of atoms relative to each other, and 6) elemental analysis by combustion to determine the relative % of carbon, hydrogen and nitrogen.

Further Aspects and Utilizations of the Invention
Therapeutic Applications

One embodiment of the present invention is to formulate prior to administration in a patient, a pharmaceutical formulation comprising *Uncaria tomentosa* (and/or its active ingredients) in one or more pharmaceutical acceptable carriers, diluents or excipients. In a preferred embodiment, a patient who has Alzheimer's disease, type II diabetes or any other amyloidosis, would orally consume commercially available *Uncaria tomentosa* in pill, tablet, caplet, soft and hard gelatin capsule, lozenge, vegicap, liquid drop, solution, syrup, tea bag, and/or bark powder form.

In another preferred embodiment *Uncaria tomentosa* obtained commercially in any form could be further modulated using suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweeting agents or flavoring agents. The compositions of the invention may be formulated so as to provide quick, sustained or delayed response of the active ingredient after administration to the patient. The compositions are preferably formulated in a unit dosage form, each dosage containing from about 1 to about 10,000 mg of *Uncaria tomentosa* (or its active ingredients), more usually about 500 to about 2,000 mg of *Uncaria tomentosa* (or its active ingredients). However, it will be understood that the therapeutic dosage administered will be determined by the physician in the light of the relevant circumstances including the clinical condition to be treated, the organ or tissues affected or suspected to be affected with amyloid accumulation, and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. For each formulation provided as an example, lowering or raising of the *Uncaria tomentosa* (or its active ingredients) concentration will cause a proportional lowering or raising of the other ingredients as indicated. Hard gelatin capsules may be prepared by using 500 mg of *Uncaria tomentosa* (or its active ingredients), 400 mg of starch, and 20 mg of magnesium stearate. The above ingredients are mixed and filled into hard gelatin capsules in 920 mg quantities.

A tablet is prepared by using 500 mg of *Uncaria tomentosa* (or its active ingredients), 800 mg of microcrystalline cellulose, 20 mg of fumed silicon dioxide and 10 mg of stearic acid. The components are blended and compressed to form tablets each weighing 1230 mg.

An aerosol solution is prepared by using 0.25 active ingredient, 29.75 ethanol, and 70 of propellent 22 (chlorodifluoromethane). The *Uncaria tomentosa* (or its active ingredients) is mixed with ethanol. The mixture is added to a portion of the Propellent 22, cooled to –30° C., and transferred to a filling device. The required amount is then fed to a stainless steel container and diluted with the remainder of the propellent. The value units (listed above) are then fitted to the container. Such an aerosol form of *Uncaria tomentosa* (or its active ingredients) may be useful for the treatment of amyloids involving the brain (such as Alzheimer's disease, Down's syndrome, prion diseases etc) by using an aerosol or nasal spray. Previous studies have suggested that in these central nervous system amyloidoses the initial form of entry of a possible environmental agent which may be playing a role in pathogenesis may be derived from the outside world through the nasal passages.

Tablets are made by using 240 mg of *Uncaria tomentosa* (or its active ingredients), 180 mg of starch, 140 mg of microcrystalline cellulose, 16 mg of polyvinylpyrrolidone (as 10% in water), 18 mg of sodium carboxymethyl starch, 2 mg of magnesium stearate and 2 mg of talc (total=600 mg). *Uncaria tomentosa* (or its active ingredients), starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No.18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 600 mg.

Capsules each containing 160 mg of medicant are made by using 160 mg of *Uncaria tomentosa* (or its active ingredients), 118 mg of starch, 118 mg of microcrystalline cellulose, and 4 mg of magnesium stearate (total=400 mg). The *Uncaria tomentosa* (or its active ingredients), cellulose, starch and magnesium stearate are blended, passed through a No. 45 mesh U.S. sieve, and filled into hard gelatin capsules in 400 mg quantities.

Suppositories each containing 225 mg of *Uncaria tomentosa* (or its active ingredients) are made by using 225 mg of *Uncaria tomentosa* (or its active ingredients), 2,000 mg of saturated fatty acid glycerides (total=2,225 mg). The *Uncaria tomentosa* (or its active ingredients) are passed through a No.60 mesh U.S. sieve and suspended in the saturated fatty acid glycerides previously melted using the minimum heat necessary. The mixture is then poured into a suppository mold of nominal 2 g capacity and allowed to cool.

Suspensions each containing 50 mg of medicant per 5 ml dose are made by using 50 mg of *Uncaria tomentosa* (or its active ingredients), 50 mg of sodium carboxymethyl cellulose, 1.25 ml of syrup, 0.10 ml of benzoic acid solution, flavor, color, and purified water to total 5 ml. The medicant is passed though a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

An intravenous formulation is prepared by using 250 mg of *Uncaria tomentosa* (or its active ingredients), and 1000 mg of isotonic saline. The solution of the above ingredients is administered intravenously at a rate of 1 ml per minute to a subject in need of treatment.

In a preferred embodiment the therapeutic compound of the invention can be administered in any pharmaceutically acceptable vehicle. As used herein "pharmaceutically acceptable vehicle" includes, but is not limited to, any and all solvents, sterile liquids, such as water and oils, including those of petroleum, animal, vegetable or synthetic origin, such as peanut oil, soybean oil, mineral oil, sesame oil and the like, dispersion media, coatings, antibacterial and antifungal agents, isotonic and adsorption delaying agents, and the like which are compatible with the activity of the compound and are physiologically acceptable to the subject. An example of a pharmaceutically acceptable vehicle is buffered normal saline (0.15 molar NaCl). The use of such media and agents for pharmaceutically active substances is well known in the art. Supplementary active compounds can also be incorporated into the compositions. Suitable pharmaceutical excipients include starch, glucose, lactose, sucrose, gelatin, malt, rice, fluor, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

In the methods of the invention, amyloid formation, deposition, accumulation and/or persistence in a subject is inhibited by administrating *Uncaria tomentosa* (or its active ingredients) in a therapeutic dosage to the subject. The term subject is intended to include living organisms in which amyloidosis can occur. Examples of subjects include humans, monkeys, cows, dogs, sheep, cats, mice, rats, and transgenic species thereof. Administration of the compositions of the present invention to a subject to be treated can be carried out using known procedures, at dosages and for periods of time effective to inhibit amyloidosis in the subject. An effective amount of the therapeutic compound necessary to achieve a therapeutic effect may vary according to factors such as the amount of amyloid already deposited at the organ or tissue site in the subject, the age, sex and weight of the subject, and the ability of the therapeutic compound to inhibit amyloid formation, deposition, accumulation, persistence, and/or to cause dissolution of pre-formed amyloid in the subject. Dosage regimens can therefore be adjusted to provide the optimum therapeutic response. For example, several divided doses may be administered daily or the dose may be proportionally reduced as indicated by the needs of the therapeutic situation. A non-limiting example of an effective dose range for *Uncaria tomentosa* (or its active ingredients) is between 10 and 1000 mg/kg of body weight/per day, but preferably 10 to 100 mg/kg of body weight.

Different modes of delivery of *Uncaria tomentosa* (or its active ingredients) may be used. Accordingly, a preferred route of administration is oral administration. Alternatively, *Uncaria tomentosa* (or its active ingredients) may be administered by other suitable routes such as subcutaneous, intravenous, intraperitoneal, all routes administered by injection. Depending on the route of administration, the active compound may be coated in a material to protect the compound from the action of acids and other natural conditions which may inactivate the compound.

To administer *Uncaria tomentosa* (or its active ingredients), it may be necessary to coat the compound with, or co-administer the compound with, a material to prevent its activation. For example, the therapeutic compound may be administered to a subject in an appropriate carrier, for example, liposomes or a diluent. Pharmaceutically acceptable diluents include saline and aqueous buffer solutions. Liposomes include water-in-oil-in-water CGF emulsions as well as conventional liposomes.

The *Uncaria tomentosa* (or its active ingredients) may also be administered parenterally or intraperitoneally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions or dispersions and sterile powders for the preparation of sterile injectable solutions or dispersion. In all cases, the composition must be sterile and must be fluid to the extent that easy use in the syringe exists. It must be stable under the conditions of manufacture and storage and must be preserved against the contaminating action of microorganisms such as bacteria and fungi. The vehicle can be a solvent or dispersion medium containing, for example, water, ethanol, polyol (for example glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, prabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the therapeutic agent plus any desired ingredients from a previously sterile-filtered solution thereof.

The *Uncaria tomentosa* (or its active ingredients) for Alzheimer's disease and other central nervous system amyloidoses may be optimized to cross the blood-brain barrier. Methods of introductions include but are not limited to systemic administration, parenteral administration i.e., via an intraperitoneal, intravenous, perioral, subcutaneous, intramuscular, intraarterial, intradermal, intramuscular, intranasal, epidural and oral routes. In a preferred embodiment, Uncaria tomentosa (or its active ingredients) may be directly administered to the cerebrospinal fluid by intraventricular injection. In a specific embodiment, it may be desirable to administer *Uncaria tomentosa* (or its active ingredients) locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment *Uncaria tomentosa* (or its active ingredients) may be delivered in a controlled release system, such as an osmotic pump. In yet another embodiment, a controlled release system can be placed in proximity to the therapeutic target, ie. the brain, thus requiring only a fraction of the systemic dose.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

INDUSTRIAL APPLICABILITY

Use of extracts from the inner bark and root parts of *Uncaria tomentosa*, and use of the ingredients contained within the various commercial preparations of *Uncaria tomentosa*, benefit human patients with Alzheimer's disease and other amyloidoses due to *Uncaria tomentosa's* newly discovered ability to inhibit amyloid fibril formation, inhibit amyloid fibril growth, inhibit amyloid-proteoglycan interactions, inhibit amyloid-glycosaminoglycan interactions, and cause dissolution and/or disruption of preformed amyloid fibrils.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

We claim:

1. A method for inhibiting the formation or persistence of brain amyloid deposits in a patient, the method comprising the step of administering to the patient a therapeutically effective amount of plant matter from a plant of the genus *Uncaria*, species *tomentosa*.

2. The method of claim 1 wherein the plant matter comprises an extract derived from the inner bark or root tissue of *Uncaria tomentosa*.

3. A method for promoting, maintaining or enhancing in a patient one or more of the mental or cognitive qualities selected from the group of mental or cognitive qualities associated with amyloid formation consisting of memory, concentration, and short term memory, the method comprising the step of administering to the patient a therapeutically effective amount of plant matter from a plant of the genus *Uncaria*, species *tomentosa*.

4. A method for reducing in a patient one or more of the mental or cognitive effects associated with amyloid formation selected from the group of mental or cognitive effects associated with amyloid formation consisting of cognitive or memory decline and mental decline, the method comprising the step of administering to the patient a therapeutically effective amount of plant matter from a plant of the genus *Uncaria*, species *tomentosa*.

5. A method for treating in a patient mental states associated with amyloid formation or persistence, the method comprising the step of administering to the patient a therapeutically effective amount of plant matter from a plant of the genus *Uncaria*, species *tomentosa*.

* * * * *

UNITED STATES PATENT AND TRADEMARK OFFICE
CERTIFICATE OF CORRECTION

| | | |
|---|---|---|
| PATENT NO. | : 6,346,280 B1 | Page 1 of 1 |
| APPLICATION NO. | : 09/198824 | |
| DATED | : February 12, 2002 | |
| INVENTOR(S) | : Castillo et al. | |

It is certified that error appears in the above-identified patent and that said Letters Patent is hereby corrected as shown below:

Please insert the following statement in Column 1 after line 9 before "TECHNICAL FIELD":

--This invention was made with Government support under AG16551 awarded by the National Institute on Aging. The Government has certain rights in the invention.--

Signed and Sealed this

Tenth Day of March, 2009

JOHN DOLL
*Acting Director of the United States Patent and Trademark Office*